(12) United States Patent
Barthe et al.

(10) Patent No.: US 10,905,900 B2
(45) Date of Patent: Feb. 2, 2021

(54) SYSTEMS AND METHODS FOR ULTRASOUND TREATMENT

(71) Applicant: Guided Therapy Systems, LLC, Mesa, AZ (US)

(72) Inventors: Peter G. Barthe, Phoenix, AZ (US); Michael H. Slayton, Tempe, AZ (US)

(73) Assignee: Guided Therapy Systems, LLC, Scottsdale, AZ (US)

( * ) Notice: Subject to any disclaimer, the term of this patent is extended or adjusted under 35 U.S.C. 154(b) by 0 days.

(21) Appl. No.: 15/368,220

(22) Filed: Dec. 2, 2016

(65) Prior Publication Data

US 2017/0080258 A1 Mar. 23, 2017

Related U.S. Application Data

(60) Continuation of application No. 14/833,865, filed on Aug. 24, 2015, now Pat. No. 9,533,174, which is a (Continued)

(51) Int. Cl.
| | |
|---|---|
| *A61N 7/00* | (2006.01) |
| *A61B 8/00* | (2006.01) |
| *A61B 8/14* | (2006.01) |
| *A61N 7/02* | (2006.01) |
| *A61B 8/13* | (2006.01) |
| *A61B 8/08* | (2006.01) |

(Continued)

(52) U.S. Cl.
CPC ................. *A61N 7/00* (2013.01); *A61B 8/13* (2013.01); *A61B 8/14* (2013.01); *A61B 8/4254* (2013.01); *A61B 8/5246* (2013.01); *A61N 7/02* (2013.01); *A61B 8/4272* (2013.01); *A61B 8/485* (2013.01); *A61B 2017/320069* (2017.08); *A61B 2018/00642* (2013.01); *A61B 2018/00898* (2013.01); *A61B 2090/378* (2016.02); *A61N 2007/006* (2013.01); *A61N 2007/0013* (2013.01); *A61N 2007/0034* (2013.01); *A61N 2007/0052* (2013.01); *A61N 2007/0065* (2013.01); *A61N 2007/0091* (2013.01); *A61N 2007/0095* (2013.01); *A61N 2007/027* (2013.01)

(58) Field of Classification Search
CPC ........... A61B 2018/00642; A61B 2018/00898; A61B 2019/5276; A61B 8/13; A61B 8/14; A61B 8/4254; A61B 8/4272; A61B 8/485; A61N 2007/0013; A61N 2007/0034; A61N 2007/006; A61N 2007/0091; A61N 2007/0095; A61N 2007/027; A61N 7/00; A61N 7/02
See application file for complete search history.

(56) References Cited

U.S. PATENT DOCUMENTS

| | | | |
|---|---|---|---|
| 2008/0058783 A1* | 3/2008 | Altshuler | A61B 18/203 606/9 |
| 2008/0183077 A1* | 7/2008 | Moreau-Gobard | A61N 7/02 600/439 |
| 2010/0198068 A1* | 8/2010 | Rivaz | A61B 8/483 600/443 |

* cited by examiner

*Primary Examiner* — Mark D Remaly
(74) *Attorney, Agent, or Firm* — Quarles & Brady LLP

(57) ABSTRACT

Various embodiments provide a method for an extended field of view treatment. The method can include the steps of imaging a region; targeting a region with directed ultrasound energy; monitoring the region; moving the imaging, treatment, and monitoring region while spatially correlating to one or more prior regions via imaging and/or position sensing; continuing the extended field of view treatment; and, achieving an ultrasound induced biological effect in the extended field of view treatment region.

14 Claims, 16 Drawing Sheets

Related U.S. Application Data division of application No. 13/136,544, filed on Aug. 2, 2011, now Pat. No. 9,149,658.

(60) Provisional application No. 61/369,793, filed on Aug. 2, 2010, provisional application No. 61/369,806, filed on Aug. 2, 2010, provisional application No. 61/370,095, filed on Aug. 2, 2010, provisional application No. 61/369,782, filed on Aug. 2, 2010.

(51) Int. Cl.
*A61B 17/32* (2006.01)
*A61B 18/00* (2006.01)
*A61B 90/00* (2016.01)

SYSTEMS AND METHODS FOR ULTRASOUND TREATMENT

CROSS-REFERENCE TO RELATED APPLICATIONS

This application is a continuation of U.S. patent application Ser. No. 14/833,865 filed Aug. 24, 2015, which is a divisional application of U.S. patent application Ser. No. 13/136,544, filed Aug. 2, 2011, now U.S. Pat. No. 9,149,658, which claims priority to and the benefit of U.S. Provisional Patent Application No. 61/369,782, entitled "Systems and Methods for Ultrasound Treatment", filed Aug. 2, 2010; U.S. Provisional Patent Application No. 61/369,793, entitled "System and Method for Treating Sports Related Injuries", filed Aug. 2, 2010; U.S. Provisional Patent Application No. 61/369,806, entitled "System and Method for Treating Sports Related Injuries", filed Aug. 2, 2010; U.S. Provisional Patent Application No. 61/370,095, entitled "System and Method for Treating Cartilage", filed Aug. 2, 2010; all of which are incorporated by reference herein.

BACKGROUND

Focused ultrasound surgery has tremendous potential compared to other energy based treatment modalities. Ultrasound energy can be placed deep into tissue at precise depths with highly controlled spatial distributions. However, one difficulty has been that the sub-millimeter or millimeter sized treatment region needs to be scanned to treat, image, or monitor a large volume or to produce fractionated treatment zones composed of multiple lesions. Attempts to address such problems have been via motorized and/or electronically scanned treat mechanisms. However, such methods and systems are limited in flexibility and coverage to the scanned volume, not only of the treatment region but regions for imaging and monitoring. Further, such methods typically require the patient to be constantly moved, such as in a magnetic resonance imaging (MRI) guided ultrasound treatment system, or alternatively the mechanism to be repositioned, with limited flexibility and accuracy. For example, if a treatment mechanism treats in a line, at fixed depth, and is scanned around the circumference of an essentially circular or curved object, such as a leg, arm, fingers, foot, etc., the lesions at the fixed depth will be spaced closer or further together, or even overlap, based on the convex or concave curvature of the surface as well as treatment depth. What is needed are new, sophisticated systems and methods for ultrasound treatment which provide increased accuracy and flexibility of treatment.

SUMMARY

Various embodiments of systems and methods for ultrasound treatment are provided. Accordingly, ultrasound treatments can include methods for soft tissue injuries and for orthopedic fibrous soft tissue surgical procedures. The ultrasound energy can be spherically, cylindrically, or otherwise focused, unfocused, or defocused and can be applied to tissue to achieve a biological effect and/or a therapeutic effect.

Various embodiments provide a system for extended field of view treatment. The system can include a hand-held probe and a controller in communication with the hand held probe. In some embodiments the probe can include a housing which can contain or is coupled to a therapy transducer, an imaging transducer, or imaging/therapy transducer, a position sensor, a communication interface and rechargeable power supply.

Various embodiments provide a method for an extended field of view treatment. The method can include the steps of imaging a region; targeting a region with directed ultrasound energy; monitoring the region; moving the imaging, treatment, and monitoring region while spatially correlating to one or more prior regions via imaging and/or position sensing; continuing the extended field of view treatment; and, achieving an ultrasound induced biological effect in the extended field of view treatment region.

DRAWINGS

The present disclosure will become more fully understood from the detailed description and the accompanying drawings, wherein.

DESCRIPTION

Figure 1:
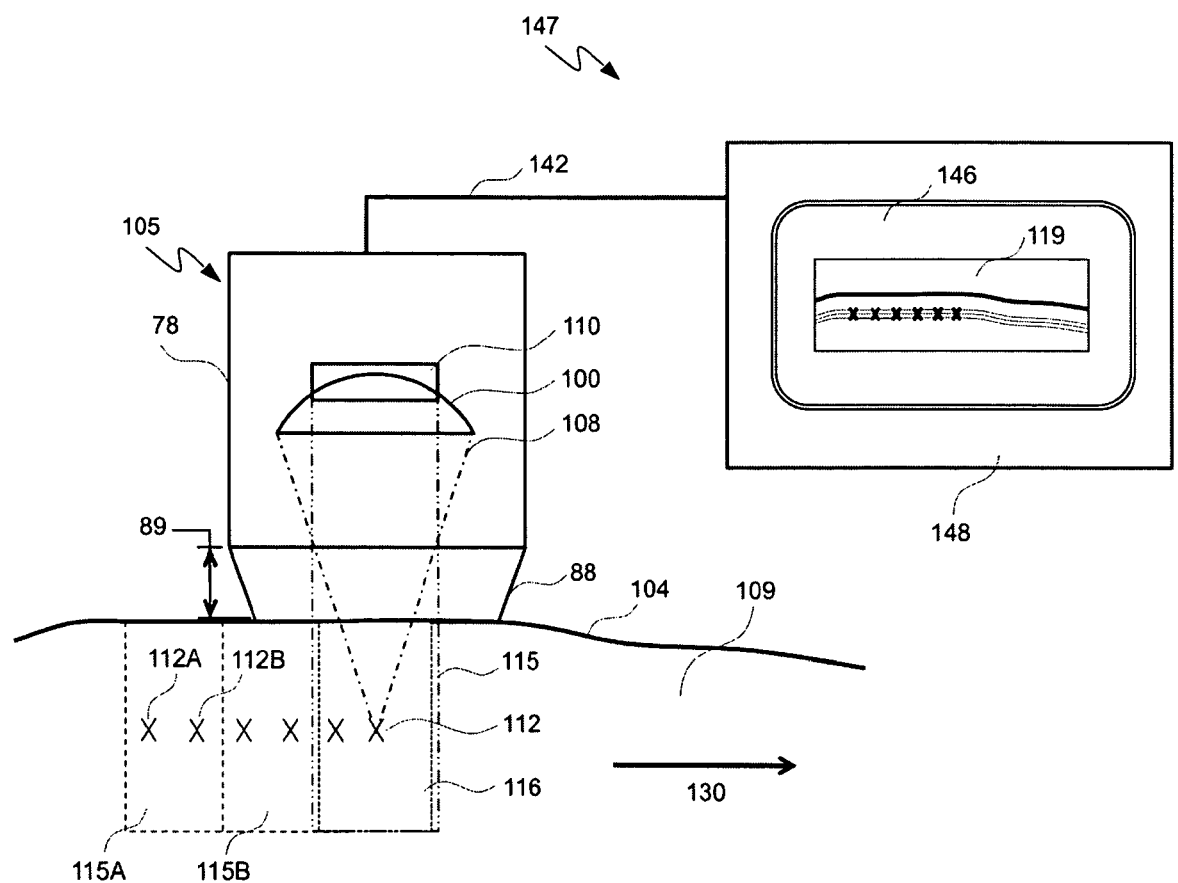
FIG. 1 illustrates a treatment system, according to various embodiments.

The following description is merely exemplary in nature and is in no way intended to limit the various embodiments, their application, or uses. As used herein, the phrase "at least one of A, B, and C" should be construed to mean a logical (A or B or C), using a non-exclusive logical or. As used herein, the phrase "A, B and/or C" should be construed to mean (A, B, and C) or alternatively (A or B or C), using a non-exclusive logical or. It should be understood that steps within a method may be executed in different order without altering the principles of the present disclosure.

The drawings described herein are for illustrative purposes only of selected embodiments and not all possible implementations, and are not intended to limit the scope of any of the various embodiments disclosed herein or any equivalents thereof. It is understood that the drawings are not drawn to scale. For purposes of clarity, the same reference numbers will be used in the drawings to identify similar elements.

The various embodiments may be described herein in terms of various functional components and processing steps. It should be appreciated that such components and steps may be realized by any number of hardware components configured to perform the specified functions. For example, various embodiments may employ various medical treatment devices, visual imaging and display devices, input terminals and the like, which may carry out a variety of functions under the control of one or more control systems or other control devices. In addition, the embodiments may be practiced in any number of medical contexts and that the various embodiments relating to a method and system for acoustic tissue treatment as described herein are merely indicative of exemplary applications for the invention. For example, the principles, features and methods discussed may be applied to any medical application. Further, various aspects of the various embodiments may be suitably applied to cosmetic applications. Moreover, some of the embodiments may be applied to cosmetic enhancement of skin and/or various subcutaneous tissue layers.

Various embodiments provide a method of ultrasound treatment. The method can include the steps of imaging a treatment region; targeting a treatment region with directed ultrasound energy; monitoring the treatment region; moving said treatment region while spatially correlating to one or more prior treatment regions via imaging or position sensing to create an extended field of view imaging, treatment, and monitoring region; continuing the extended field of view treatment; and achieving at least one ultrasound induced biological effect in the extended field of view treatment region.

In one embodiment, the method can include ultrasound imaging. In one embodiment, the method can include directing ultrasound energy that is spherically focused, cylindrically focused, multi-focused, unfocused, or defocused to produce a therapeutic or surgical result. In one embodiment, the method can include image correlation. In one embodiment, the method can include position sensor data processing. In one embodiment, the method can include dynamically targeting a treatment region with directed ultrasound energy based on information from an extended field of view imaging, treatment, or monitoring region.

In one embodiment, the method can include comprising creating thermally or mechanically induced ultrasound bioeffects with directed ultrasound energy at or adjacent to the treatment region, including effects of heating, coagulation, ablation, cavitation, streaming, radiation force, increased perfusion, inflammation, generation of heat shock proteins, and initiation of healing cascade. In one embodiment, the method can include targeting a treatment region with a non-flat surface.

Various embodiments provide a system for ultrasound treatment. The system can include a hand-held probe comprising: a housing containing or coupled to: an ultrasound transducer configured to deliver directed ultrasound energy; an ultrasound transducer configured to create ultrasound images, including monitoring images, of a treatment region and surrounding tissue; a position sensor configured to communicate a position of the housing versus time; a communication interface configured for wired or wireless communication; and a controller in communication with the communication interface, configured to form and correlate images, process position data, create an extended field of view imaging, treatment, and monitoring region, and control delivery of directed ultrasound energy to the extended field of view treatment region to achieve at least one ultrasound induced biological effect.

In one embodiment, the system can include a hand held housing with a rechargeable battery. In one embodiment, the system can include a hand held housing with switches, and displays. In one embodiment, the position sensor is an optical, laser, laser Doppler, mechanical, or magnetic position sensor. In one embodiment, the ultrasound is transducer configured to deliver directed ultrasound energy, which is focused, multi-focused, un-focused, or defocused array of one or more elements.

In one embodiment, the system can include comprising a display configured to display an extended field of view image, an extended field of view treatment map, or an extended field of view monitoring image.

In various embodiments, treatment comprises, but is not limited to, any desired biological effect due to thermally induced or mechanically induced ultrasound bioeffects at or adjacent to the treatment region. These include heating, coagulation, ablation, cavitation, streaming, radiation force, increased perfusion, inflammation, generation of heat shock proteins, and initiation of healing cascade, among others.

In various embodiments, treatment produces a therapeutic effect in a region of interest ("ROI"). A therapeutic effect can be cauterizing and repairing a portion of a subcutaneous tissue layer. A therapeutic effect can be stimulating or increase an amount of heat shock proteins. Such a therapeutic effect can cause white blood cells to promote healing of a portion of a subcutaneous tissue layer in the ROI. A therapeutic effect can be peaking inflammation in a portion of the ROI to decrease pain at the injury location. A therapeutic effect can be creating lesion to restart or increase the wound healing cascade at the injury location. A therapeutic effect can be increasing the blood perfusion to the injury location. Such a therapeutic effect would not require ablative ultrasound energy. A therapeutic effect can be encouraging collagen growth. A therapeutic effect can be relieving pain. A therapeutic effect may increase the "wound healing" response through the liberation of cytokines and may produce reactive changes within the tendon and muscle itself, helping to limit surrounding tissue edema and decrease the inflammatory response to tendon injury.

A therapeutic effect can be healing an injury to in a subcutaneous tissue layer. Therapeutic effects can be combined. A therapeutic effect can be synergetic with the medicant administered to ROI. A therapeutic effect may be an enhanced delivery of a medicant administered to ROI. A therapeutic effect may increase an amount of a medicant administered to ROI. A therapeutic effect may be stimulation of a medicant administered to ROI. A therapeutic effect may be initiation of a medicant administered to ROI. A therapeutic effect may be potentiation of a medicant administered to ROI.

A therapeutic effect can be produced by a biological effect that initiated or stimulated by the ultrasound energy. A biological effect can be stimulating or increase an amount of heat shock proteins. Such a biological effect can cause white blood cells to promote healing of a portion of a tissue layer. A biological effect can be to restart or increase the wound healing cascade at the injury location. A biological effect can be increasing the blood perfusion to the injury location. A biological effect can be encouraging collagen growth at the injury location. A biological effect may increase the liberation of cytokines and may produce reactive changes within a portion of a tissue layer. A biological effect may by peaking inflammation in a portion of a tissue layer. A biological effect may at least partially shrinking collagen in a portion of a tissue layer. A biological effect may be denaturing of proteins in ROI.

A biological effect may be creating immediate or delayed cell death (apoptosis) in a portion of a tissue layer. A biological effect may be collagen remodeling a portion of a tissue layer, A biological effect may be the disruption or modification of biochemical cascades in a portion of a tissue layer. A biological effect may be the production of new collagen in a portion of a tissue layer. A biological effect may a stimulation of cell growth in a portion of a tissue layer. A biological effect may be angiogenesis in a portion of a tissue layer. A biological effect may a cell permeability response in a portion of a tissue layer.

A biological effect may be an enhanced delivery of medicants to a portion of a issue layer. A biological effect may increase an amount of a medicant in a portion of a tissue layer. A biological effect may be stimulation of a medicant in a portion of a tissue layer. A biological effect may be initiation of a medicant in a portion of a tissue layer. A biological effect may be potentiation of a medicant in a portion of a tissue layer.

With reference to FIG. 1, an extended field of view treatment system 147 is illustrated, according to various embodiments. Ultrasound probe 105 is in communications with treatment controller 148 via interface 142. Interface 142 can be a wired connection, a wireless connection or combinations thereof. In various embodiments, ultrasound probe 105 comprises therapy transducer array 100, and imaging transducer array 110. In various embodiments, therapy transducer array 100 is a transducer array comprising at least one active transduction element. In various embodiments, imaging transducer array 110 is a transducer array comprising at least one active imaging transduction element.

Ultrasound probe 105 can comprise enclosure 78, which can contain therapy transducer array 100, and imaging transducer array 110. In one embodiment, enclosure 78 is designed for comfort and control while used in an operator's hand. Enclosure 78 may also contain various electronics, EEPROM, switches, interface connections, motion mechanisms, acoustic coupling means, cooling means, thermal monitoring, and/or memory for holding programs.

Ultrasound probe 105 can comprise tip 88. Tip 88 can be coupled to enclosure 78. In one embodiment, tip 88 is disposable, and for example EEPROM determines if tip 88 has been used and can regulate further usage based upon prior usage. In some embodiments, tip 88 has height 89, which can control depth of therapeutic ultrasound energy 108 into subcutaneous tissue 109. In some embodiments, a plurality of tips 88, each having a different height 89 may be used to direct therapeutic ultrasound energy 108 to a plurality of depths in subcutaneous tissue 109.

Ultrasound probe 105 can be coupled to skin surface 104 to image and treat and monitor subcutaneous tissue 109. Subcutaneous tissue 109 can be any tissue that is below skin surface 104. For example, subcutaneous tissue 109 can include, is not limited to, any of: epidermal layer, dermis layer, fat layer, cellulite, SMAS, a gland, a portion of hair, connective tissue, muscle, tendon, cartilage, or an organ, and combinations thereof. In various embodiments, therapeutic ultrasound energy 108 can be emitted by therapy transducer array 100 to create at least one treatment zone 112 in subcutaneous tissue 109. In various embodiments imaging ultrasound energy can be emitted and received by at least one of imaging transducer array 110 and therapy transducer array 100 to create a treatment monitoring area 116 in subcutaneous tissue 109. In one embodiment, imaging ultrasound energy can be emitted and received by imaging transducer array 110 to create an imaging area 115 in subcutaneous tissue 109. In various embodiments, monitoring area 116 can be a specialized signal-processing version of ultrasound imaging area 115, and thus where not explicitly mentioned, monitoring area 116 is implicitly included in the specification with reference to an imaging area 115.

In other embodiments ultrasound probe 105 is coupled to other tissue surfaces, such as an organ, as opposed to skin surface 104, to image, treat, and monitor subcutaneous tissue 109, such as the organ. For example, therapy transducer array 100 and imaging transducer array 110 can be integrated to or attached to a tool, such as, for example, an arthroscopic tool, laparoscopic tool, or an endoscopic tool that may be inserted into a patient's body with minimal invasiveness.

In various embodiments, ultrasound probe 105 can be moved in a direction 130, by hand or mechanism, to form a spatial sequence of the imaging area 115, namely image sequence 115A, 115B . . . , 115n, and a spatial sequence of the monitoring area 116, namely monitoring sequence 116A, 116B, . . . 116n, and so on. Overlapping images of image sequence 115A, 115B, . . . 115n can be combined in treatment system via image processing techniques into an extended image 119, and rendered on display 146. The image sequence 115A, 115B . . . 115n provides real-time spatial position information such that as ultrasound probe 105 is moved 130, treatment system may trigger and create a spatial sequence of the treatment zone 112, namely treatment sequence 112A, 112B, . . . 112n and so on. The extended field of view treatment sequence that is formed may constitute any preferred disposition of treatment lesions, such as multiple quantities, sizes, depths, types, etc. In addition, the monitoring sequence 116A, 116B, . . . 116n can be combined into an extended monitoring image 121, overlaid, adjacent to, and analogous to extended image 119 for use as treatment feedback and/or display. The extended monitoring image 121 can be a specialized signal-processing version of extended image 119, and thus where not explicitly mentioned or annotated, extended monitoring image 121 is implicitly included in the specification with reference to an extended image 119. The extended field of view treatment sequence depth and position information can be overlaid atop the extended image 119 and shown on display 146. The extended images 119, extended treatment maps 150, extended treatment sequences 112, and extended monitoring images can be 2-D, 3-D or 4-dimensional. In various embodiments the extended image 119 provides information to dynamically, precisely, and accurately dispose a plurality of lesions 25, such as an equispaced plurality of lesions 25, even while scanning the surface of convex, concave, ellipsoidal, circular, essentially circular and other bodies of rotation, surfaces which closely represent human skin, appendages, and organs.

Therapeutic ultrasound energy 108 creates treatment zone 112 in a tissue layer, at which a temperature of tissue is raised to at least 43° C., or is raised to a temperature in the range form about 43° C. to about 100° C., or from about 50° C. to about 90° C. or from about 55° C. to about 75° C., or from about 50° C. to about 65° C. or from about 60° C. to about 68° C.

In various embodiments, the ultrasound energy level for ablating fibrous soft tissue layer is in the range of about 0.1 joules to about 500 joules in order to create an ablative lesion. However, the therapeutic ultrasound energy 108 level can be in the range of from about 0.1 joules to about 100 joules, or from about 1 joules to about 50 joules, or from about 0.1 joules to about 10 joules, or from about 50 joules to about 100 joules, or from about 100 joules to about 500 joules, or from about 50 joules to about 250 joules.

Further, the amount of time ultrasound energy is applied at these levels to create a lesion varies in the range from approximately 1 millisecond to several minutes. However, the ranges can be from about 1 millisecond to about 5 minutes, or from about 1 millisecond to about 1 minute, or from about 1 millisecond to about 30 seconds, or from about 1 millisecond to about 10 seconds, or from about 1 millisecond to about 1 second, or from about 1 millisecond to about 0.1 seconds, or about 0.1 seconds to about 10 seconds, or about 0.1 seconds to about 1 second, or from about 1 millisecond to about 200 milliseconds, or from about 1 millisecond to about 0.5 seconds.

The frequency of the ultrasound energy can be in a range from about 0.1 MHz to about 100 MHz, or from about 0.1 MHz to about 50 MHz, or from about 1 MHz to about 50 MHz or about 0.1 MHz to about 30 MHz, or from about 10 MHz to about 30 MHz, or from about 0.1 MHz to about 20 MHz, or from about 1 MHz to about 20 MHz, or from about 20 MHz to about 30 MHz.

The frequency of the ultrasound energy is in the range from about 0.1 MHz to about 50 MHz, or about 0.1 MHz to about 30 MHz, or from about 10 MHz to about 30 MHz, or from about 0.1 MHz to about 20 MHz. or from about 20 MHz to about 30 MHz, or from about 5 MHz to about 15 MHz, or from about 2 MHz to about 12 MHz or from about 3 MHz to about 7 MHz.

In some embodiments, the ultrasound energy can be emitted to depths at or below a skin surface in a range from about 0 mm to about 150 mm, or from about 0 mm to about 100 mm, or from about 0 mm to about 50 mm, or from about 0 mm to about 30 mm, or from about 0 mm to about 20 mm, or from about 0 mm to about 10 mm, or from about 0 mm to about 5 mm. In some embodiments, the ultrasound energy can be emitted to depths below a skin surface in a range from about 5 mm to about 150 mm, or from about 5 mm to about 100 mm, or from about 5 mm to about 50 mm, or from about 5 mm to about 30 mm, or from about 5 mm to about 20 mm, or from about 5 mm to about 10 mm. In some embodiments, the ultrasound energy can be emitted to depths below a skin surface in a range from about 10 mm to about 150 mm, or from about 10 mm to about 100 mm, or from about 10 mm to about 50 mm, or from about 10 mm to about 30 mm, or from about 10 mm to about 20 mm, or from about 0 mm to about 10 mm.

In some embodiments, the ultrasound energy can be emitted to depths at or below a skin surface in the range from about 20 mm to about 150 mm, or from about 20 mm to about 100 mm, or from about 20 mm to about 50 mm, or from about 20 mm to about 30 mm. In some embodiments, the ultrasound energy can be emitted to depths at or below a skin surface in a range from about 30 mm to about 150 mm, or from about 30 mm to about 100 mm, or from about 30 mm to about 50 mm. In some embodiments, the ultrasound energy can be emitted to depths at or below a skin surface in a range from about 50 mm to about 150 mm, or from about 50 mm to about 100 mm. In some embodiments, the ultrasound energy can be emitted to depths at or below a skin surface in a range from about 20 mm to about 60 mm, or from about 40 mm to about 80 mm, or from about 10 mm to about 40 mm, or from about 5 mm to about 40 mm, or from about 0 mm to about 40 mm, or from about 10 mm to about 30 mm, or from about 5 mm to about 30 mm, or from about 0 mm to about 30 mm.

In various embodiments, a temperature of tissue receiving the ultrasound energy can be in a range from 30° C. to about 100° C., or from 43° C. to about 60° C., or from 50° C. to about 70° C., or from 30° C. to about 50° C. or from 43° C. to about 100° C., or from 33° C. to about 100° C. or from 30° C. to about 65° C., or from 33° C. to about 70° C. as well as variations thereof. Alternatively, the targeted skin surface and the layers above a target point in the subcutaneous layer are heated to a 10° C. to 15° C. above the tissue's natural state.

In various embodiments, therapy transducer array 100 may comprise one or more transduction elements 125 for facilitating treatment. Transduction element 125 may comprise piezoelectrically active material, such as lead zirconate titanate (PZT), or other piezoelectrically active material such as, but not limited to, a piezoelectric ceramic, crystal, plastic, and/or composite materials, as well as lithium niobate, lead titanate, barium titanate, and/or lead metaniobate. In addition to, or instead of, a piezoelectrically active material. Therapy transducer array 100 may comprise any other materials configured for generating radiation and/or acoustical energy. Therapy transducer array 100 may also comprise one or more matching and/or backing layers configured along with the transduction element 125, such as being coupled to the piezoelectrically active material. Therapy transducer array 100 may also be configured with single or multiple damping elements along the transduction element 125.

Moreover, in some embodiments, any variety of mechanical lenses or variable focus lenses, such as, for example, liquid-filled lenses, may also be used to focus and or defocus the energy field. For example, therapy transducer array 100 may also be configured with an electronic focusing array in combination with one or more transduction elements 125 to facilitate increased flexibility in treating a region of interest ("ROI") in subcutaneous tissue 109. Array may be configured in a manner similar to therapy transducer array 100. That is, array may be configured as an array of electronic apertures that may be operated by a variety of phases via variable electronic time delays. Accordingly, the electronic apertures of array may be manipulated, driven, used, configured to produce and/or deliver energy in a manner corresponding to the phase variation caused by the electronic time delay. For example, these phase variations may be used to deliver defocused beams, planar beams, focused beams including spherically or cylindrically focused, and/or multi-focused beams, each of which may be used in combination to achieve different physiological effects in treatment region 112, including mechanically and thermally induced ultrasound bioeffects in subcutaneous tissue 109.

In various embodiment, ultrasound probe 105 is configured with the ability to controllably produce conformal distribution of elevated temperature in soft tissue within ROI 115 through precise spatial and temporal control of acoustic energy deposition, i.e., control of ultrasound probe 105 is confined within selected time and space parameters, with such control being independent of the tissue. The ultrasound energy 120 can be controlled to produce a conformal distribution of elevated temperature in soft tissue within ROI 115 using spatial parameters. The ultrasound energy 120 can be controlled to produce conformal distribution of elevated temperature in soft tissue within ROI 115 using temporal parameters. The ultrasound energy 120 can be controlled to produce a conformal distribution of elevated temperature in soft tissue within ROI 115 using a combination of spatial parameters and temporal parameters. In some embodiments, a conformal distribution of elevated temperature in soft tissue within ROI 115 is conformal region of elevated temperature in ROI 115.

In various embodiments, conformal region of elevated temperature can create a lesion in ROI 113. In various embodiments, conformal region of elevated temperature can initiate thermal injury in a portion of ROI 115. In various embodiments, conformal region of elevated temperature 25 can initiate or stimulate coagulation in a portion of ROI 115. In various embodiments, conformal region of elevated temperature can be one of a series of micro scoring in ROI 115. In various embodiments, conformal region of elevated temperature can with a first ultrasound energy deposition and a second energy deposition.

Shaped conformal distribution of elevated temperature can be created through adjustment of the strength, depth, and type of focusing, energy levels and timing cadence. For example, focused ultrasound can be used to create precise arrays of microscopic thermal ablation zones. Ultrasound energy 120 can produce an array of ablation zones deep into the layers of the soft tissue. Detection of changes in the reflection of ultrasound energy can be used for feedback control to detect a desired effect on the tissue and used to control the exposure intensity, time, and/or position.

In various embodiment, ultrasound probe 105 is configured with the ability to controllably produce conformal distribution of elevated temperature in soft tissue within ROI 115 through precise spatial and temporal control of acoustic energy deposition, i.e., control of ultrasound probe 105 is confined within selected time and space parameters, with such control being independent of the tissue. The ultrasound energy 120 can be controlled using spatial parameters. The ultrasound energy 120 can be controlled using temporal parameters. The ultrasound energy 120 can be controlled using a combination of temporal parameters and spatial parameters.

In accordance with various embodiments, control system and ultrasound probe 105 can be configured for spatial control of ultrasound energy 120 by controlling the manner of distribution of the ultrasound energy 120. For example, spatial control may be realized through selection of the type of one or more transducer configurations insonifying ROI 115, selection of the placement and location of ultrasound probe 105 for delivery of ultrasound energy 120 relative to ROI 115 e.g., ultrasound probe 105 being configured for scanning over part or whole of ROI 115 to produce contiguous thermal injury having a particular orientation or otherwise change in distance from ROI 115, and/or control of other environment parameters, e.g., the temperature at the acoustic coupling interface can be controlled, and/or the coupling of ultrasound probe 105 to tissue. Other spatial control can include but are not limited to geometry configuration of ultrasound probe 105 or transducer assembly, lens, variable focusing devices, variable focusing tens, stand-offs, movement of ultrasound probe, in any of six degrees of motion, transducer backing, matching layers, number of transduction elements in transducer, number of electrodes, or combinations thereof.

In various embodiments, control system and ultrasound probe 105 can also be configured for temporal control, such as through adjustment and optimization of drive amplitude levels, frequency, waveform selections, e.g., the types of pulses, bursts or continuous waveforms, and timing sequences and other energy drive characteristics to control thermal ablation of tissue. Other temporal control can include but are not limited to full power burst of energy, shape of burst, timing of energy bursts, such as, pulse rate duration, continuous, delays, etc., change of frequency of burst, burst amplitude, phase, apodization, energy level, or combinations thereof.

The spatial and/or temporal control can also be facilitated through open-loop and closed-loop feedback arrangements, such as through the monitoring of various spatial and temporal characteristics. As a result, control of acoustical energy within six degrees of freedom, e.g., spatially within the X, Y and Z domain, as well as the axis of rotation within the XY, YZ and XZ domains, can be suitably achieved to generate conformal distribution of elevated temperature of variable shape, size and orientation. For example, through such spatial and/or temporal control, ultrasound probe 105 can enable the regions of elevated temperature possess arbitrary shape and size and allow the tissue to be heated in a controlled manner.

Figure 2:
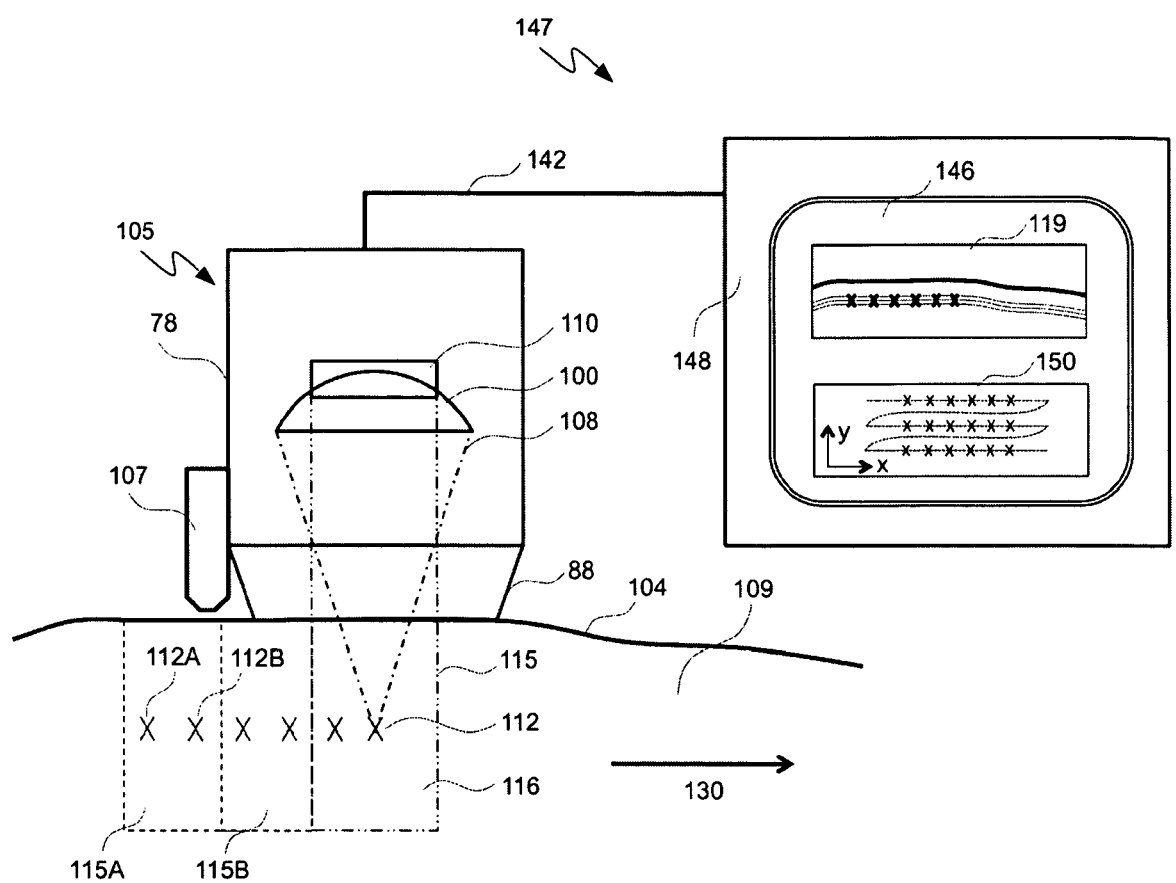
FIG. 2 illustrates a treatment system, according to various embodiments.

With reference to FIG. 2, a treatment system is illustrated, according to various embodiments. Ultrasound probe 105 is in communications with treatment controller 148 via interface 142. Interface 142 can be a wired connection, a wireless connection or combinations thereof. In various embodiments, ultrasound probe 105 comprises therapy transducer array 100, imaging transducer array 110, and position sensor 107. Ultrasound probe 105 can comprise enclosure 78, which can contain therapy transducer array 100, imaging transducer array 110, and position sensor 107.

Position sensor 107 can be integrated into ultrasound probe 105 or attached to ultrasound probe 105. In one embodiment, position sensor 107 is an optical sensor measuring 1-D, 2-D, or 3-D movement 130 of ultrasound probe 105 versus time while probe travels along skin surface 104. Such a position sensor may control treatment sequence 112A, 112B, . . . 112$n$ directly, by using position information in the treatment system to trigger treatment. In various embodiments, therapy can be triggered when the ultrasound probe 105 reaches a fixed or pre-determined range away from the last treatment zone 112. Speed of motion can be used to control therapeutic ultrasound energy 108. For example, if the motion is too fast information can be provided to the user to slow down and/or energy can be dynamically adjusted within limits. Position information may also be used to suppress energy if crossing over the same, spatial position, if desired. Such a position sensor 107 may also determine if ultrasound probe 105 is coupled to skin surface 104, to safely control energy delivery and provide information to users. Position sensor data acquisition can be synchronized with imaging sequence and monitoring sequence, to geo-tag and arrange the image frames 115A, 115B, . . . 115$n$ and so on, in the correct spatial orientation to form an extended image 119, or likewise extended monitoring image 121, for display 146.

Extended position versus time data can be stored as tracking information, 123, and linked with the extended treatment sequence, 112A, 112B, . . . 112$n$, and may be rendered as a graphical treatment map 150 and rendered on display 146. Treatment map 150 can be displayed as 2-D or multidimensional data, and can be real-time. In various embodiments a spherically focused therapy array 100, such as an annular array, is moved in a time varying and/or position varying direction 130, captured by position sensor 107, and/or recorded by image 115, and processed into an extended image 119, extended treatment map 150, and extended monitoring image 121. In some embodiments, all extended images, extended monitoring images, treatment sequences, and treatment maps can be stored and played back as movies, images, or electronic records. Treatment map 150 can be used to illustrate where treatment has occurred and/or to help the user fill-in untreated areas, especially if the user cannot see the treatment surface. In one embodiment a projector can be used to overlay the treatment map atop the treatment surface, or the treatment map can be superimposed atop other visualizations of the treatment surface With further reference to FIGS. 1 and 2, treatment system, according to various embodiments, is illustrated. In various embodiments, treatment system comprises controller 148, display 146, ultrasound probe 105, and interface 142 for communication between ultrasound probe 105 and controller 148. Ultrasound probe 105 may be controlled and operated by controller 148, which also relays and processes images obtained by ultrasound probe 105 to display 146. In one embodiment, controller 148 is capable of coordination and control of the entire treatment process to achieve the desired therapeutic effect on ROI. For example, in one embodiment, controller 148 may comprise power source components, sensing and monitoring components, one or more RF driver circuits, cooling and coupling controls, and/or processing and control logic components. Controller 148 may be configured and optimized in a variety of ways with more or less subsystems and components to implement treatment system for controlled targeting of a portion of subcutaneous tissue 109, and the various embodiments illustrated in FIGS. 1 and 2 are merely for illustration purposes.

For example, for power sourcing components, controller 148 may comprise one or more direct current (DC) power supplies capable of providing electrical energy for the entire controller 148, including power required by a transducer electronic amplifier/driver. A DC current sense or voltage sense device may also be provided to confirm the level of power entering amplifiers/drivers for safety and monitoring purposes.

In one embodiment, amplifiers/drivers may comprise multi-channel or single channel power amplifiers and/or drivers. In one embodiment for transducer array configurations, amplifiers/drivers may also be configured with a beamformer to facilitate array focusing. An exemplary beamformer may be electrically excited by an oscillator/digitally controlled waveform synthesizer with related switching logic.

Power sourcing components may also comprise various filtering configurations. For example, switchable harmonic filters and/or matching may be used at the output of amplifier/driver to increase the drive efficiency and effectiveness. Power detection components may also be included to confirm appropriate operation and calibration. For example, electric power and other energy detection components may be used to monitor the amount of power entering ultrasound probe 105.

Various sensing and monitoring components may also be implemented within controller 148. For example, in one embodiment, monitoring, sensing, and interface control components may be capable of operating with various motion detection systems implemented within ultrasound probe 105, to receive and process information such as acoustic or other spatial and temporal information from ROI. Sensing and monitoring components may also comprise various controls, interfacing, and switches and/or power detectors. Such sensing and monitoring components may facilitate open-loop and/or closed-loop feedback systems within extended field of view treatment system 147.

In one embodiment, sensing and monitoring components may further comprise a sensor that may be connected to an audio or visual alarm system to prevent overuse of system. In this embodiment, the sensor may be capable of sensing the amount of energy transferred to the skin, and/or the time that extended field of view treatment system 147 has been actively emitting energy. When a certain time or temperature threshold has been reached, the alarm may sound an audible alarm, or cause a visual indicator to activate to alert the user that a threshold has been reached. This may prevent overuse of treatment system 146. In one embodiment, the sensor may be operatively connected to controller 148 and force controller 148, to stop emitting therapeutic ultrasound energy 108 from ultrasound probe 105.

Additionally, an exemplary controller 148 may further comprise a system processor and various digital control logic, such as one or more of microcontrollers, microprocessors, field-programmable gate arrays, computer boards, and associated components, including firmware and control software, which may be capable of interfacing with user controls and interfacing circuits as well as input/output circuits and systems for communications, displays, interfacing, storage, documentation, and other useful functions. System software may be capable of controlling all initialization, timing, level setting, monitoring, safety monitoring, and all other system functions required to accomplish user-defined treatment objectives. Further, various control switches, touch panels, multi-touch panels, capacitive and inductive switches, may also be suitably configured to control operation.

With reference again to FIGS. 1 and 2, an exemplary extended field of view treatment system 147 also may comprise display 146 capable of providing images of ROI in various embodiments where ultrasound energy may be emitted from ultrasound probe 105 in a manner for imaging. In one embodiment, display 146 is a computer monitor. Display 146 may be capable of enabling the user to facilitate localization of treatment area and surrounding structures. In an alternative embodiment, the user may know the location of the specific subcutaneous tissue layer 109 to be treated based at least in part upon prior experience or education and without display 146. In another embodiment, display 146 also includes a touch screen to allow user touch- or multi-touch input in a graphical user interface. In yet another embodiment display 146 is a 3-D display.

After localization, therapeutic ultrasound energy 108 is delivered at a depth, distribution, timing, and energy level to achieve the desired therapeutic effect at ROI to treat injury. Before, during and/or after delivery of therapeutic ultrasound energy 108, monitoring of the treatment area and surrounding structures may be conducted to further plan and assess the results and/or provide feedback to controller 148, and to a system operator via display 146.

Feedback information may be generated or provided by any one or more acoustical sources, such as B-scan images, A-lines, Doppler or color flow images, surface acoustic wave devices, hydrophones, elasticity measurement, or shear wave based devices. In addition, optical sources can also be utilized, such as video and/or infrared cameras, laser Doppler imagers, optical coherence tomography imagers, and temperature sensors. Further, feedback information can also be provided by semiconductors, such as thermistors or solid state temperature sensors, by electronic and electromagnetic sensors, such as impedance and capacitance measurement devices and/or thermocouples, and by mechanical sensors, such as stiffness gages, strain gages or stress measurement sensors, or any suitably combination thereof. Moreover, various other switches, acoustic or other sensing mechanisms and methods may be employed to enable transducer array 100 to be acoustically coupled to one or more ROI.

With reference to FIG. 1, a transducer array is illustrated, according to various embodiments. Accordingly, therapy transducer array 100 comprises a plurality of transduction elements 125. As illustrated, plurality of transduction elements 125 can be curved to operably focus therapeutic ultrasound energy 108 to treatment zone 112. However, plurality of transduction elements 125 is not limited to only focusing therapeutic ultrasound energy 108. For example, plurality of transduction elements 123 may emit therapeutic ultrasound energy 108 in an unfocused matter. In a further example, plurality of transduction elements 125 may emit therapeutic ultrasound energy 108 in a defocused matter. In some embodiments, some of the plurality of transduction elements 125 may emit therapeutic ultrasound energy 108 that is focused to treatment zone 112, while some of the plurality of transduction elements 125 may emit at least one of unfocused and defocused therapeutic ultrasound energy 108, while some transduction elements 125 may emit no energy.

In some embodiments, some of the plurality of transduction elements 125 may emit therapeutic ultrasound energy 108 that is focused to treatment zone 112 to a first depth and some of the plurality of transduction elements 125 may emit therapeutic ultrasound energy 108 that is focused to treatment zone 112 to a second depth. Further, some of the plurality of transduction elements 125 may emit therapeutic ultrasound energy 108 that is focused to treatment zone 112 to a first depth, some of the plurality of transduction elements 125 may emit therapeutic ultrasound energy 108 that is focused to treatment zone 112 to a second depth, and some of the plurality of transduction elements 125 may emit therapeutic ultrasound energy 108 that is focused to treatment zone 112 to a third depth and so on. The quantity of different depths is unlimited via electronic control of the plurality of transduction elements 125.

Plurality of transduction elements 125 can be arranged in a linear configuration. The number of transduction elements 125 in the therapy transducer array 100 is unlimited. Imaging transducer array 110 may be positioned in the center of transducer array 100. Imaging transducer array 110 emits ultrasound energy and received reflected ultrasound energy in order to provide an image. Imaging area 115 is defined by characteristics of imaging transducer array 110, such as, for example, frequency, size, shape, number of elements, mechanical and/or electronic focusing.

Figure 4:
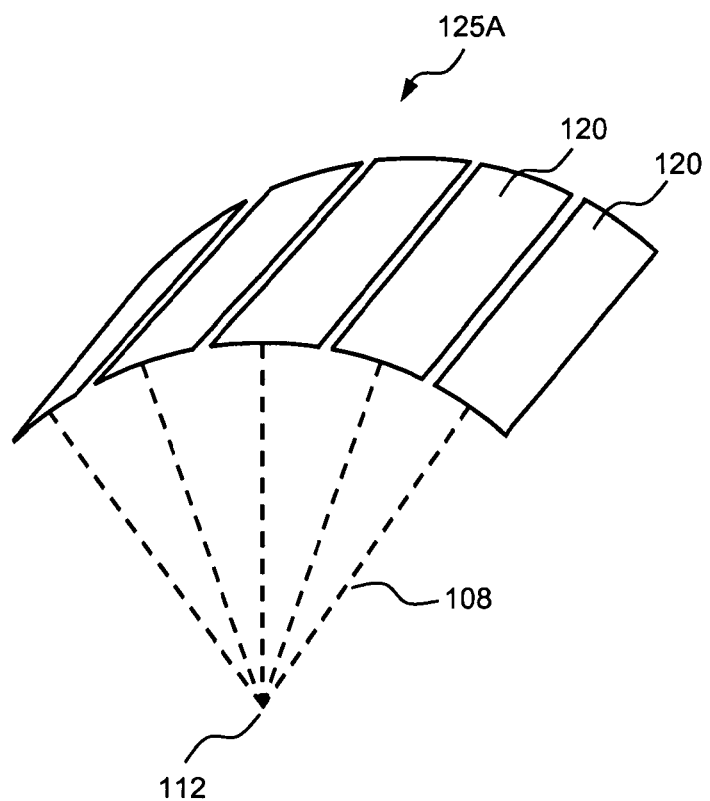
FIG. 4 illustrates an embodiment of a transduction element, according to various embodiments.

Now turning to FIG. 4, an alternative embodiment of transduction element 125 is illustrated. Transduction element 125A comprises an array of smaller transduction elements 120. Each of the individual smaller transduction elements 120 can be separately controlled. For example, each of the individual smaller transduction elements 120 may emit therapeutic ultrasound energy 108 at different frequencies. For example, each of the individual smaller transduction elements 120 may emit therapeutic ultrasound energy 108 for different time periods. For example, each of the individual smaller transduction elements 120 may emit therapeutic ultrasound energy 108 at different power levels. In some embodiments, each of the individual smaller transduction elements 120 may be controlled to emit therapeutic ultrasound energy 108 in any combination of different frequencies, different time periods, and different power levels. Of course, each of the transduction elements 125A in therapy transducer array 100 can be controlled such that each of the individual smaller transduction elements 120 each of the in transduction elements 125A may be controlled to emit therapeutic ultrasound energy 108 in any combination of different frequencies, different time periods, and different power levels.

In some embodiments, each of the individual smaller transduction elements 120 may be controlled in a combination of different frequencies, different time periods, and different power levels to focus therapeutic ultrasound energy 108 to treatment zone 112 and focus therapeutic ultrasound energy 108 to a second treatment zone.

Figure 5:
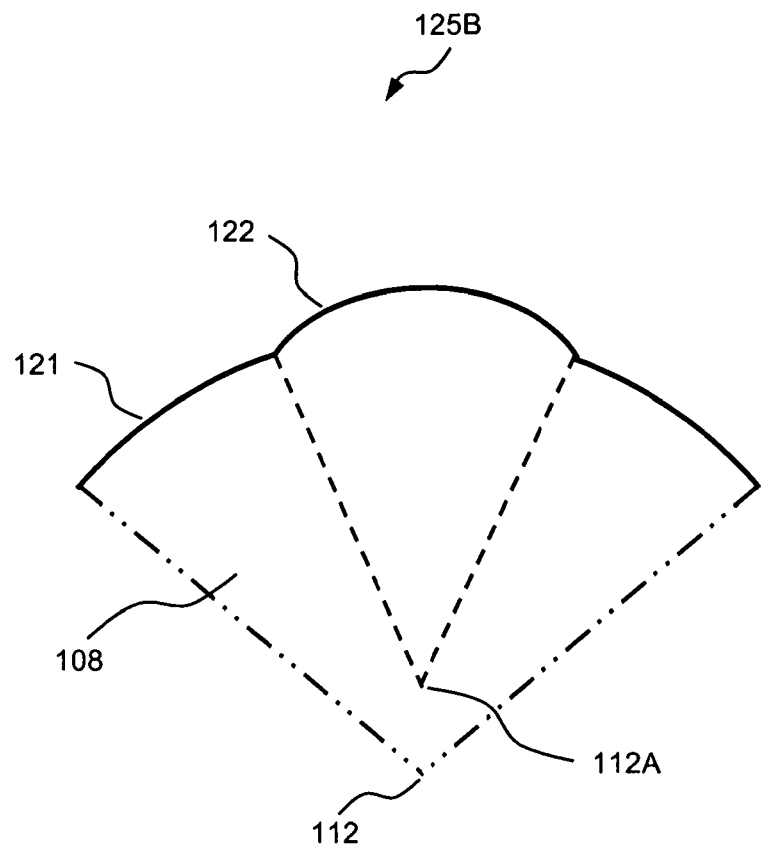
FIG. 5 illustrates an embodiment of a transduction element, according to various embodiments.

With reference to FIG. 5, an alternative embodiment of transduction element 125 is illustrated. Transduction element 125B comprises first transduction element 121 and second transduction element 122. In some embodiments, first transduction element 121 and second transduction element 122 can have the same focus, which can be mechanical focus, electronic focus, or combinations thereof. In some embodiments, first transduction element 121 and second transduction element 122 can have different focus, which can be mechanical focus, electronic focus, or combinations thereof. In some embodiments, first transduction element 121 and second transduction element 122 can be multiple elements of the same therapy transducer, sectioned for different f-numbers.

In some embodiments, first transduction element 121 is operable to focus therapeutic ultrasound energy 108 to treatment zone 112 and second transduction element 122 is operable to focus therapeutic ultrasound energy 108 to second treatment zone 112A. Alternatively, first transduction element 121 and second transduction element 122 may be controlled in a combination of different frequencies, different time periods, and different power levels to focus therapeutic ultrasound energy 108 to at least one of treatment zone 112 and second treatment zone 112A.

Figure 6:
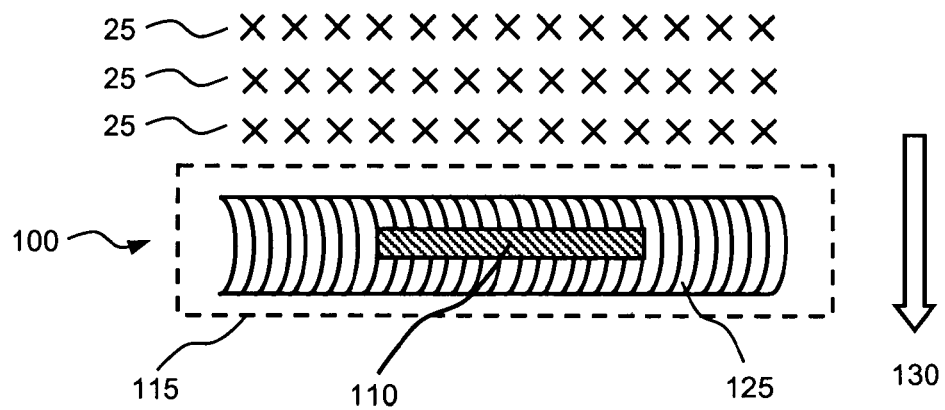
FIG. 6 illustrates a method of creating a multi-dimensional array of lesions, according to various embodiments.

Now referring to FIG. 6, a method of creating multidimensional matrix of lesions is illustrated. In some embodiments, therapy transducer array 100 can be moved in direction 130 to provide a plurality of lesions 25 in a layer of subcutaneous tissue 109. In various embodiments, a plurality of lesions 25 can be placed a 2-D pattern as illustrated in FIG. 6.

However, if therapy transducer array 100 is configured with transduction element 125A, a 3-D pattern of a plurality of lesions 25 can be created. For example, each of the individual smaller transduction elements 120 may be controlled in a combination of different frequencies, different depths, different time periods, and different power levels to focus therapeutic ultrasound energy 108 to treatment zone 112 and focus therapeutic ultrasound energy 108 to a second treatment zone 112A as the therapy transducer array 100 is moved indirection 130.

Further, if therapy transducer array 100 is configured with transduction element 125B, a 3-D pattern of a plurality of lesions 25. For example, first transduction element 121 is operable to focus therapeutic ultrasound energy 108 to treatment zone 112 and second transduction element 122 is operable to focus therapeutic ultrasound energy 108 to second treatment zone 112A as therapy transducer array 100 is moved in direction 130.

Figure 7:
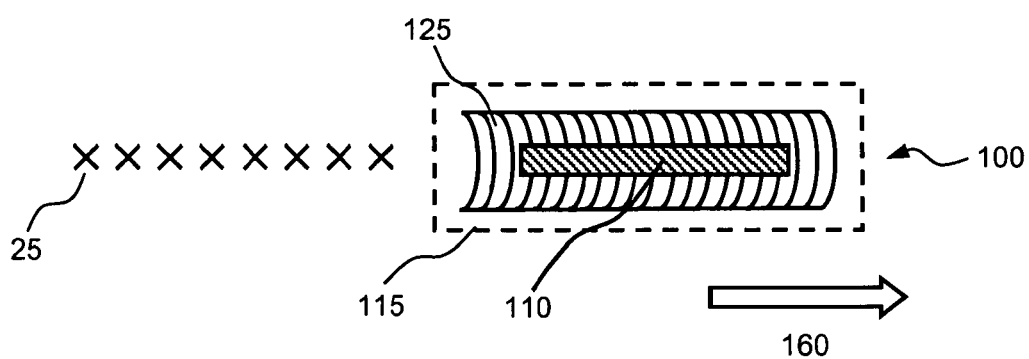
FIG. 7 illustrates a method of creating a linear array of lesions, according to various embodiments.

With reference to FIG. 7, a method of creating linear matrix of lesions is illustrated. In some embodiments, therapy transducer array 100 can be moved in direction 160 to provide a plurality of lesions 25 in a layer of subcutaneous tissue 109. In various embodiments, a plurality of lesions 25 can be placed a linear pattern as illustrated in FIG. 7.

However, if therapy transducer array 100 is configured with transduction element 125A, a 2-D pattern of a plurality of lesions 25 can be created. For example, each of the individual smaller transduction elements 120 may be controlled in a combination of different frequencies, different time periods, and different power levels to focus therapeutic ultrasound energy 108 to treatment zone 112 and focus therapeutic ultrasound energy 108 to a second treatment zone 112A as the therapy transducer array 100 is moved in direction 160.

Further, if therapy transducer array 100 is configured with transduction element 125B, a 2-D pattern of a plurality of lesions 25 can be created. For example, first transduction element 121 is operable to focus therapeutic ultrasound energy 108 to treatment zone 112 and second transduction element 122 is operable to focus therapeutic ultrasound energy 108 to second treatment zone 112A as transducer array 100 is moved in direction 160.

Figure 8:
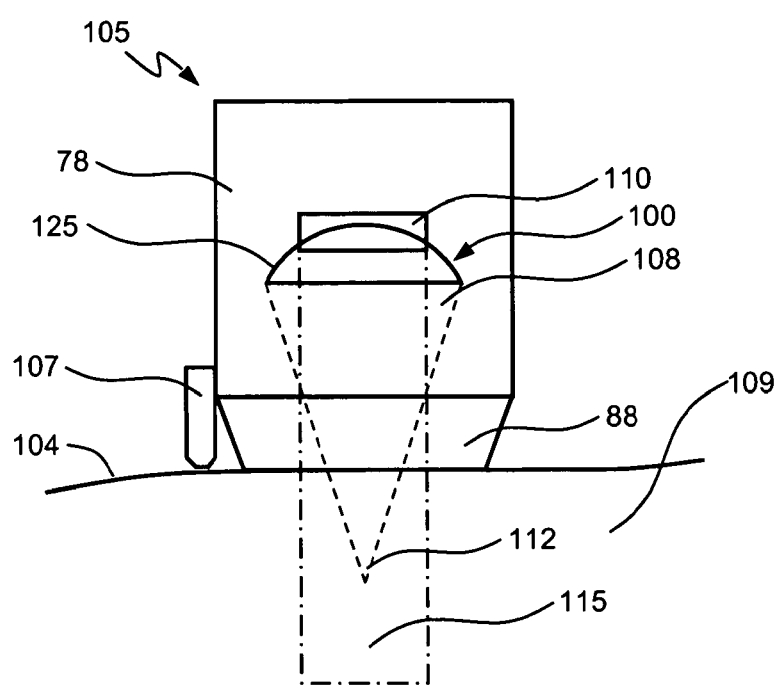
FIG. 8 illustrates an ultrasound probe, according to various embodiments.
Figure 9:
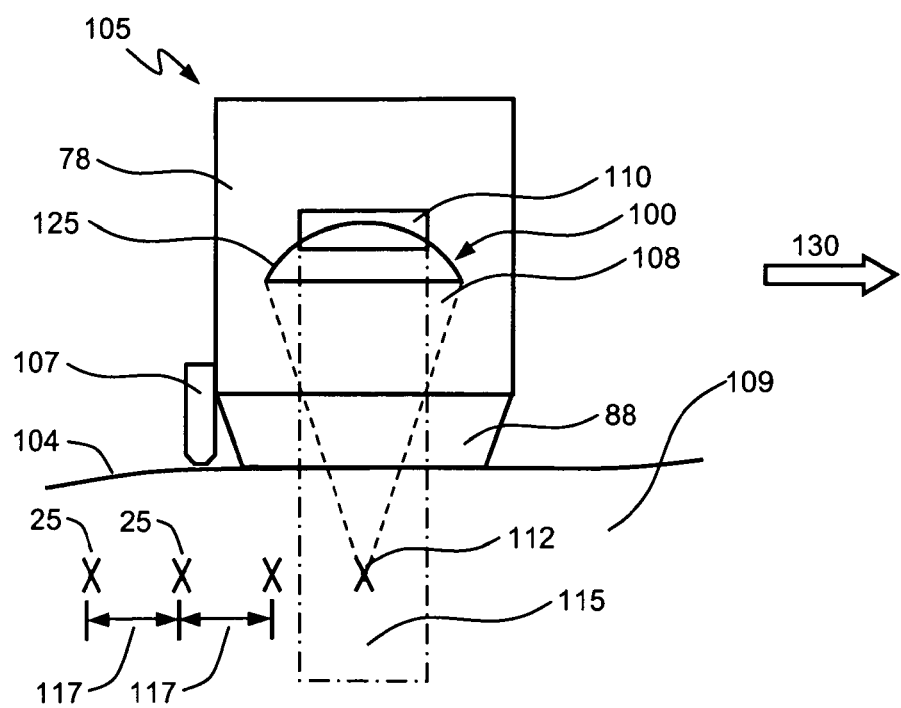
FIG. 9 illustrates an ultrasound probe, according to various embodiments.
Figure 10:
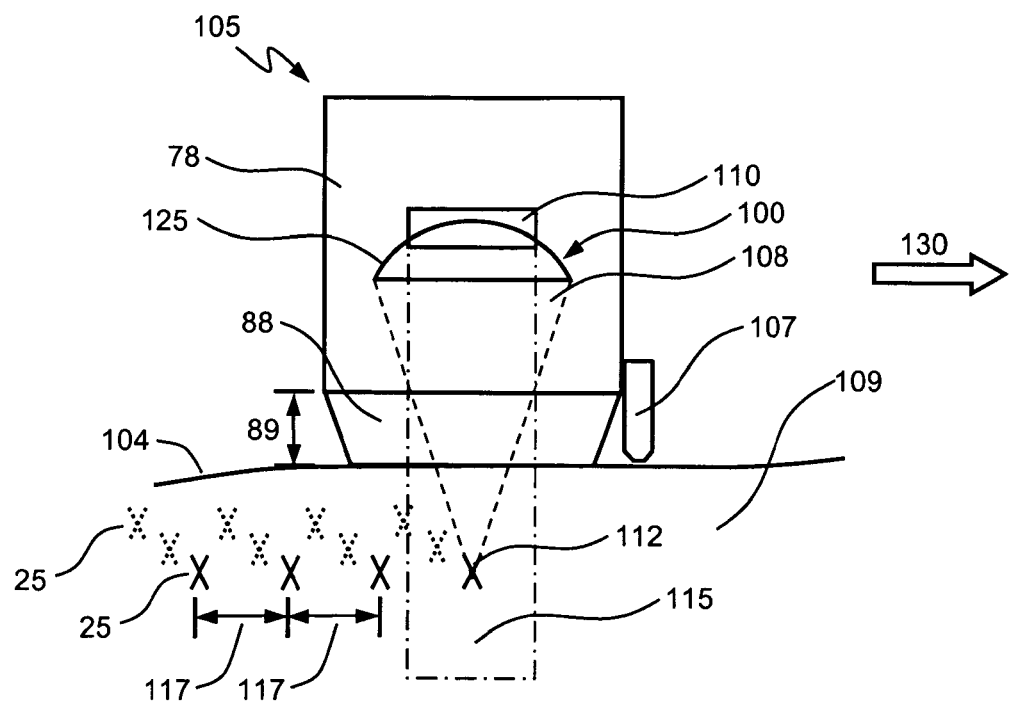
FIG. 10 illustrates an ultrasound probe, according to various embodiments.

Moving to FIGS. 8-10, ultrasound probe 105 is illustrated. In various embodiments, ultrasound probe 105 comprises enclosure 78 containing therapy transducer array 100 and imaging transducer array 110. Ultrasound probe 105 can be coupled to skin surface 104. Therapeutic ultrasound energy 108 can be emitted by therapy transducer array 100 to create treatment zone 112 in subcutaneous tissue 109. In various embodiments, therapeutic ultrasound energy 108 can create treatment zone 112.

In various embodiments, therapy transducer array 100, imaging transducer array 100, and optionally position sensor 107 can be held within enclosure 78. In one embodiment, enclosure 78 is designed for comfort and control while used in an operator's hand. Enclosure 78 may also contain various electronics, EEPROM, interface connections, motion mechanisms, and/or memory for holding programs.

Ultrasound probe 105 can comprise tip 88 that can be disposed of after contacting one or more patients. Tip 88 can be coupled to enclosure 78. In one embodiment, tip is disposable, and for example EEPROM determines if tip 88 has been used and will not allow treatment to begin tip 88 that has been previously used. In some embodiments, tip 88 has height 89 which can control therapeutic ultrasound energy 108 depth into subcutaneous tissue layer 109. In some embodiments, a plurality of tips 88, each having a different height 89 may be used to direct therapeutic ultrasound energy 108 to a plurality of depths in subcutaneous tissue layer 109.

Therapy transducer array 100 may further comprise a functional tip 88, or area at the end of the therapy transducer array 100 that emits therapeutic ultrasound energy 108. This reflective surface may enhance, magnify, or otherwise change therapeutic ultrasound energy 108 emitted from ultrasound probe 105.

A variety of embodiments of creating lesions patterns are described herein. However, in various embodiments, ultrasound probe 105 comprises position sensor 107. Position sensor 107 can be integrated into ultrasound probe 105 or attached to ultrasound probe 105. In one embodiment, position sensor 107 is a motion sensor measuring position of ultrasound probe 105. Such a motion sensor can calculate distance traveled along skin surface 104. Such a motion sensor may determine a speed of movement of ultrasound probe 105 along skin surface 104 and determine if the speed is accurate for treatment. For example if the speed is too fast, motion sensor can signal an indicator to slow the speed and/or can signal therapy transducer 100 to stop emitting therapeutic ultrasound energy 108.

In various embodiments, position sensor 107 comprises a visual element such as a camera or video capture device. In such embodiments, skin surface 104 can be geotagged. Features on the skin surface, such as, for example, a scar, a nipple, a belly button, a mole, an ankle, a knee cap, a hip bone, a mark, a tattoo, or combinations thereof and the like, may be geotagged using position sensor 107. A geotagged feature may be useful for treatment. A geotagged feature may be useful for setting parameters for treatment. A geotagged feature may be useful for determining progress or success of treatment. A geotagged feature may be useful to position ultrasound probe for a second treatment of injury location. A geotagged feature can be stored with other treatment parameters and/or treatment results.

In various embodiments, position sensor 107 can include a laser position sensor. In various embodiments position sensor 107 can include a Doppler laser position sensor. In various embodiments, position sensor can include a 3D magnetic sensor. For example, optical position sensor 107 can track position like a computer mouse that uses a laser sensor as opposed to an older version of a mouse with a roller ball. Position sensor 107 can communicate position data versus time to a display to track a position of ultrasound probe 105, such as, for example, overlaid on an image of ROI, overlaid on an image of skin surface 104, as referenced to geotagged features, as reference to injury location, as referenced to a prior treatment, and combinations thereof. In an exemplary a treatment plan can include a movement pattern of ultrasound probe 105. Such a movement pattern can be displayed and the position sensor 107 can track a position of ultrasound probe 105 during treatment as compared to the movement pattern. Tracking ultrasound prone 105 with position sensor and comparing the tracked movement to a predetermined movement may be useful as a training tool. In one embodiment, laser position sensor con geotag a feature on skin surface 104.

In various embodiments, position sensor 107 may determine a distance 117 between pulses of therapeutic ultrasound energy 108 to create a plurality of lesions 25 which are evenly spaced or disposed in any spatial configuration in one-, two-, or three-dimensions. As ultrasound probe 105 is moved in direction 160, position sensor 107 determines distance 117, regardless of a speed that ultrasound probe 105 is move, at which a pulse of therapeutic ultrasound energy 108 is to be emitted in to ROI. In various embodiments ultrasound probe 105 is triggered automatically via a timer, and in combination with a position sensor 107 to assure motion.

In various embodiments, ultrasound probe 105 can comprise a tissue contact sensor. In one embodiment, tissue contact sensor communicates whether ultrasound probe 105 is coupled to the ROI 115. The tissue contact sensor may measure a capacity of a skin surface 104 above the ROI 115 and communicate a difference between the capacity of the contact to the skin surface 104 and the capacity of air. In one embodiment, the tissue contact sensor is initiated or turned on by pressing ultrasound probe 105 against skin surface 104.

In various embodiments, position sensor 107 and extended image 119 may determine a distance 117 between pulses of therapeutic ultrasound energy 108 to create a plurality of lesions 25 which are evenly spaced or disposed in any spatial configuration in one-, two-, or three-dimensions. In various embodiments the extended image 119 alone, and/or with a 2D or 3D position sensor 107 alone provide information to precisely and accurately dispose a plurality of lesions 25, such as equispaced plurality of lesions 25, even while scanning the surface of convex, concave, ellipsoidal, circular, essentially circular and other bodies of rotation, surfaces which closely represent human skin, appendages, and organs.

Position sensor 107 may be located behind a transducer, in front of a transducer array, or integrated into a transducer array. Ultrasound probe 105 may comprise more than one position sensor 107, such as, for example, a laser position sensor and a motion sensor, or a laser position sensor and a visual device, or a motion sensor and a visual device, or a laser position sensor, a motion sensor, and a visual device. Additional embodiments of position sensor 107 may be found in U.S. Pat. No. 7,142,905, entitled "Visual Imaging System for Ultrasonic Probe" issued Nov. 28, 2006, and U.S. Pat. No. 6,540,679, entitled "Visual Imaging System for Ultrasonic Probe" issued Apr. 1, 2003, both of which are incorporated by reference.

In some embodiments, ROI comprises a portion of subcutaneous tissue 109. In some embodiments, ROI can comprise skin surface 104 and at least a portion of subcutaneous tissue. In some embodiments, ultrasound probe 105 images at least a portion of one of skin surface 104 and a portion of subcutaneous tissue 109. In one embodiment, ultrasound probe 105 images at least a portion of subcutaneous tissue 109. Ultrasound probe 105 emits therapeutic ultrasound energy 108 to at least a portion of subcutaneous tissue 109. In various embodiments, therapeutic ultrasound energy 108 treats a portion of subcutaneous tissue 109.

In some embodiments, ultrasound probe 105 can be moved in at least one direction 130 to provide a plurality of lesions 25 in subcutaneous tissue 109. In various embodiments, a plurality of lesions 25 can be placed in a pattern in a portion of subcutaneous tissue 109, such as, for example, a 1-D pattern, a 2-D pattern, a 3-D pattern, or combinations thereof. In one embodiment, therapeutic ultrasound energy 108 ablates a portion subcutaneous tissue 109 creating lesion 25. In one embodiment, therapeutic ultrasound energy 108 ablates a portion of subcutaneous tissue 109 creating lesion 25. In one embodiment, therapeutic ultrasound energy 108 coagulates a portion of subcutaneous tissue 109.

In one embodiment, ultrasound probe 105 comprises a single transduction element 125 and while emitting therapeutic ultrasound energy 108 in a pulsed matter, is moved in a linear motion along skin surface 104 to create a 1-D pattern of a plurality of lesions 25 in at least one tissue layer. In one embodiment, ultrasound probe 105 comprises a linear array of transduction elements 125 and while emitting therapeutic ultrasound energy 108 in a pulsed matter, is moved along the linear vector of the array on skin surface 104 to create a 1-D pattern of a plurality of lesions 25 in at least one tissue layer.

In one embodiment, ultrasound probe 105 comprises a linear array of transduction elements 125 and while emitting therapeutic ultrasound energy 108 in a pulsed matter, is moved along the non-linear vector of the array on skin surface 104 to create a 2-D pattern of a plurality of lesions 25 in at least one tissue layer. In one embodiment, ultrasound probe 105 comprises an array of transduction elements 125 and while emitting therapeutic ultrasound energy 108 in a pulsed matter, is moved along skin surface 104 to create a 2-D pattern of a plurality of lesions 25 in at least one tissue layer.

Figure 11:
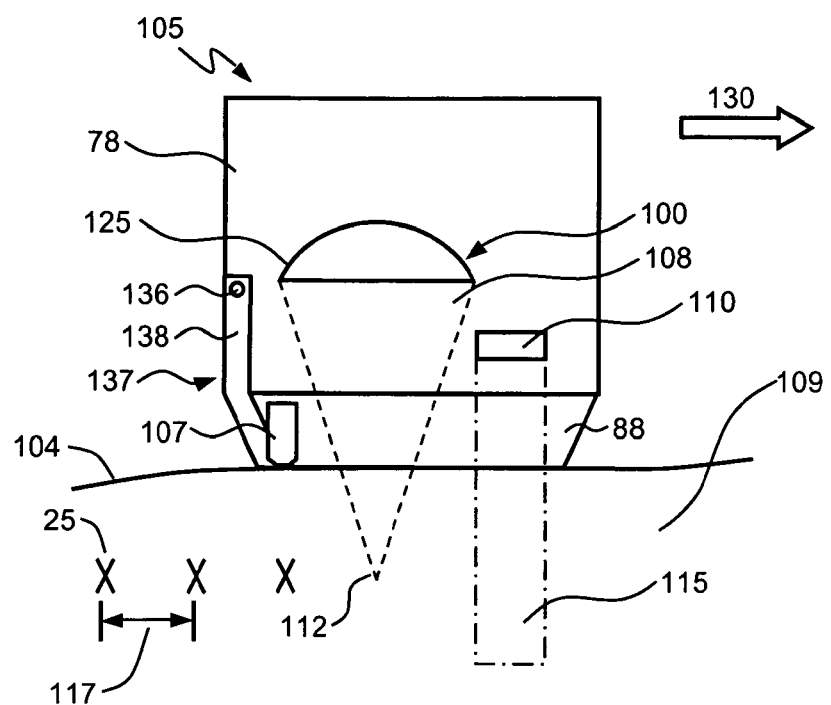
FIG. 11 illustrates an ultrasound probe, according to various embodiments.

Now with reference to FIG. 11, ultrasound probe 105 is illustrated. In various embodiments, ultrasound probe 105 comprises enclosure 78 containing therapy transducer array 100. Ultrasound probe 105 can be coupled to skin surface 104. Therapeutic ultrasound energy 108 can be emitted by therapy transducer array 100 to create treatment zone 112 in subcutaneous tissue 109. In various embodiments, therapeutic ultrasound energy 108 can create treatment zone 112.

In various embodiments, therapy transducer array 100, imaging transducer array 100, and optionally position sensor 107 can be held within enclosure 78. In one embodiment, enclosure 78 is designed for comfort and control while used in an operator's hand. Enclosure 78 may also contain various electronics, EEPROM, interface connections, motion mechanisms, and/or ram for holding programs.

In some embodiments, holder 137 operable to hold tip 88 to enclosure 78. Holder can comprise clip 138 and pivot 136. The holder 137 can be moved away from enclosure 78, so that tip 88 can be removed. Clip 138 holds tip 88 to enclosure 78. In one embodiment, holder 137 can comprise position sensor 107. In some embodiments, enclosure 78 comprises therapy transducer array 100. However, in other embodiments enclosure comprises therapy transducer array 100.

Figure 12:
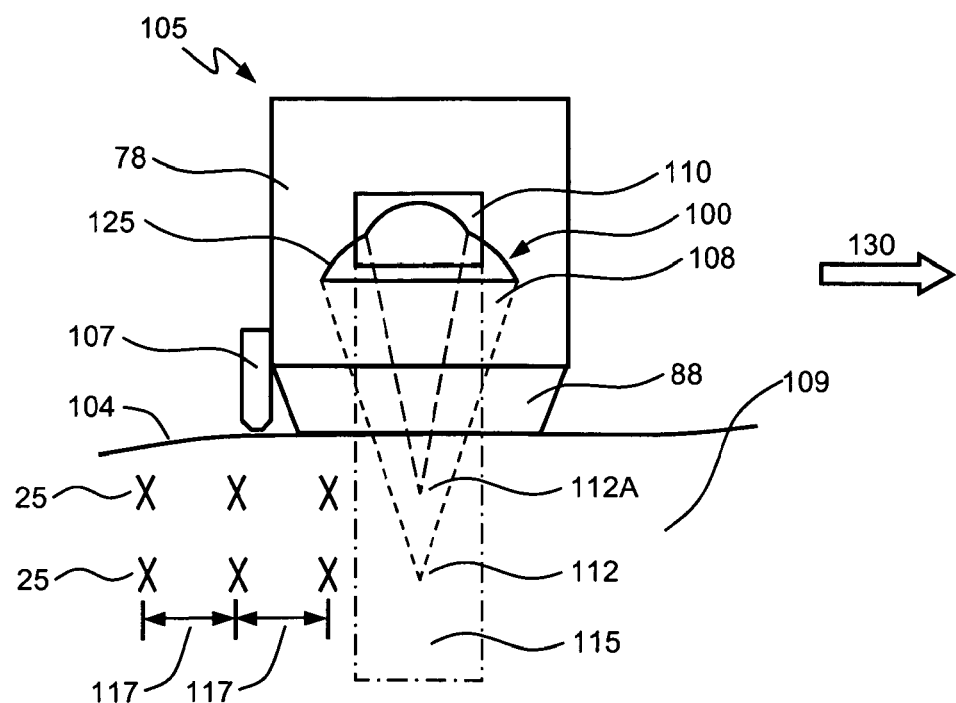
FIG. 12 illustrates an ultrasound probe, according to various embodiments.

Now with reference to FIG. 12, ultrasound probe 105 is illustrated. In various embodiments, ultrasound probe 105 comprises enclosure 78 containing therapy transducer array 100, imaging transducer array 110, and optionally position sensor 107. Therapy transducer array 100 comprises at least one transducer element 125B. Ultrasound probe 105 can be coupled to skin surface 104. Therapeutic ultrasound energy 108 can be emitted by therapy transducer array 100 to create treatment zone 112 and second treatment zone 112A in subcutaneous tissue 109. In various embodiments, therapeutic ultrasound energy 108 can create treatment zone 112 and second treatment zone 112A.

Figure 13:
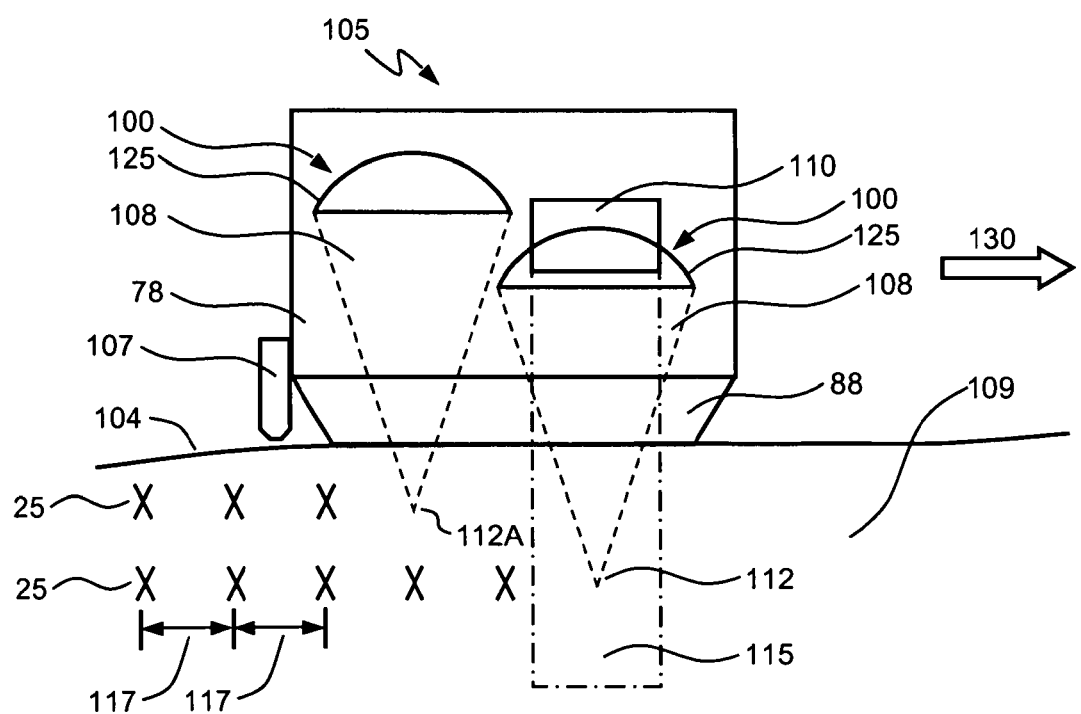
FIG. 13 illustrates an ultrasound probe comprising multiple transducers, according to various embodiments.

Referring to FIG. 13, ultrasound sound probe that comprises two therapy transducer arrays is illustration according to various embodiments. Accordingly, ultrasound probe 105 comprises a first therapy transducer array 100 and a second therapy transducer array 100. Imaging transducer array 110 can be integrated to at least one of first therapy transducer array 100 and second therapy transducer array 100. In some embodiments, first therapy transducer array 100 and second therapy transducer array 100 create treatment zone 112 and second treatment zone 112A.

Figure 14:
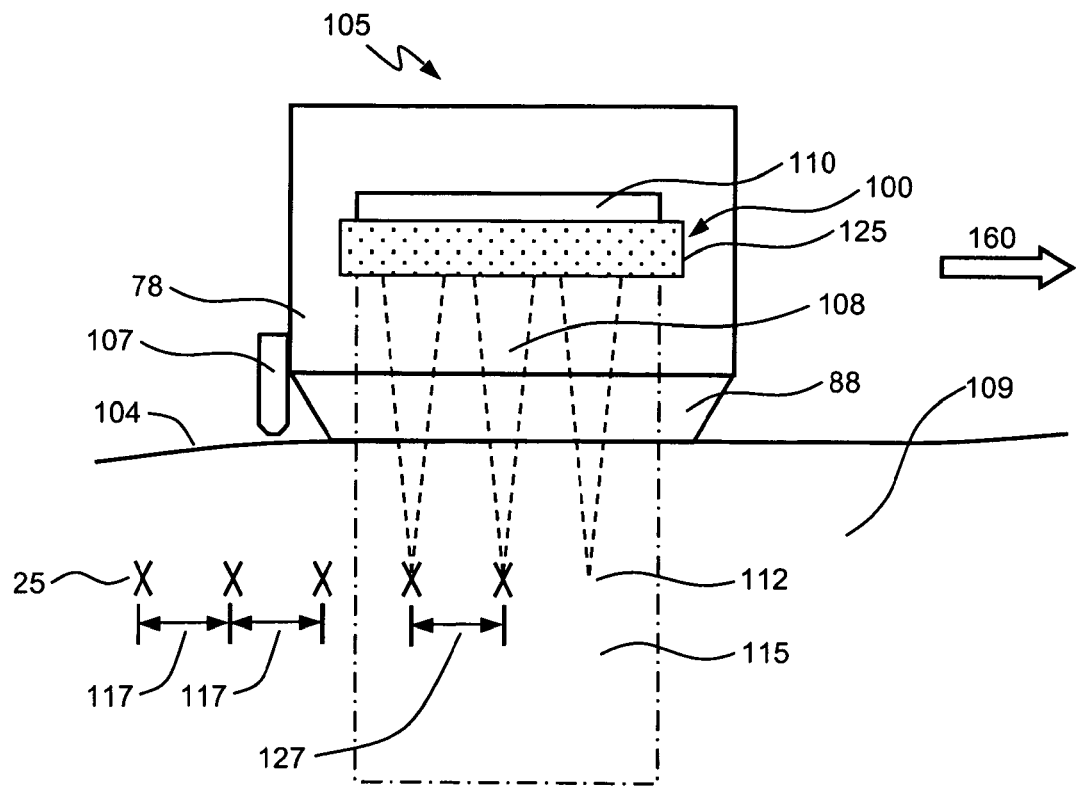
FIG. 14 illustrates a method of creating a linear array of lesions, according to various embodiments.

Moving to FIG. 14, a method of creating linear matrix of lesions is illustrated. In some embodiments, therapy transducer array 100 can be moved in direction 160 to provide a plurality of lesions 25 in a layer of subcutaneous tissue 109. In various embodiments, position sensor 107 may determine a distance 117 between pulses of therapeutic ultrasound energy 108 to create a plurality of lesions 25 which are evenly spaced or disposed in any spatial configuration in 1-D or 2-D patterns. As ultrasound probe 105 is moved in direction 160, position sensor 107 determines distance 117, regardless of a speed that ultrasound probe 105 is move, at which a pulse of therapeutic ultrasound energy 108 is to be emitted in to ROI. In some embodiments, distance 117 between lesions 25 can be less than distance 127 between treatment zones 112 of neighboring transduction elements 125. Further, therapy array 100 can be moved in orthogonal direction 130, or in any direction and angular attitude versus time.

However, if therapy transducer array 100 is configured with transduction element 125A, a 2-D pattern of a plurality of lesions 25 can be created. For example, each of the individual smaller transduction elements 120 may be controlled in a combination of different frequencies, different time periods, and different power levels to focus therapeutic ultrasound energy 108 to treatment zone 112 and focus therapeutic ultrasound energy 108 to a second treatment zone 112A as the therapy transducer array 100 is moved indirection 160.

Further, if therapy transducer array 100 is configured with transduction element 125B, a 2-D pattern of a plurality of lesions 25 can be created. For example, first transduction element 121 is operable to focus therapeutic ultrasound energy 108 to treatment zone 112 and second transduction element 122 is operable to focus therapeutic ultrasound energy 108 to second treatment zone 112A as transducer array 100 is moved in direction 160.

Figure 15:
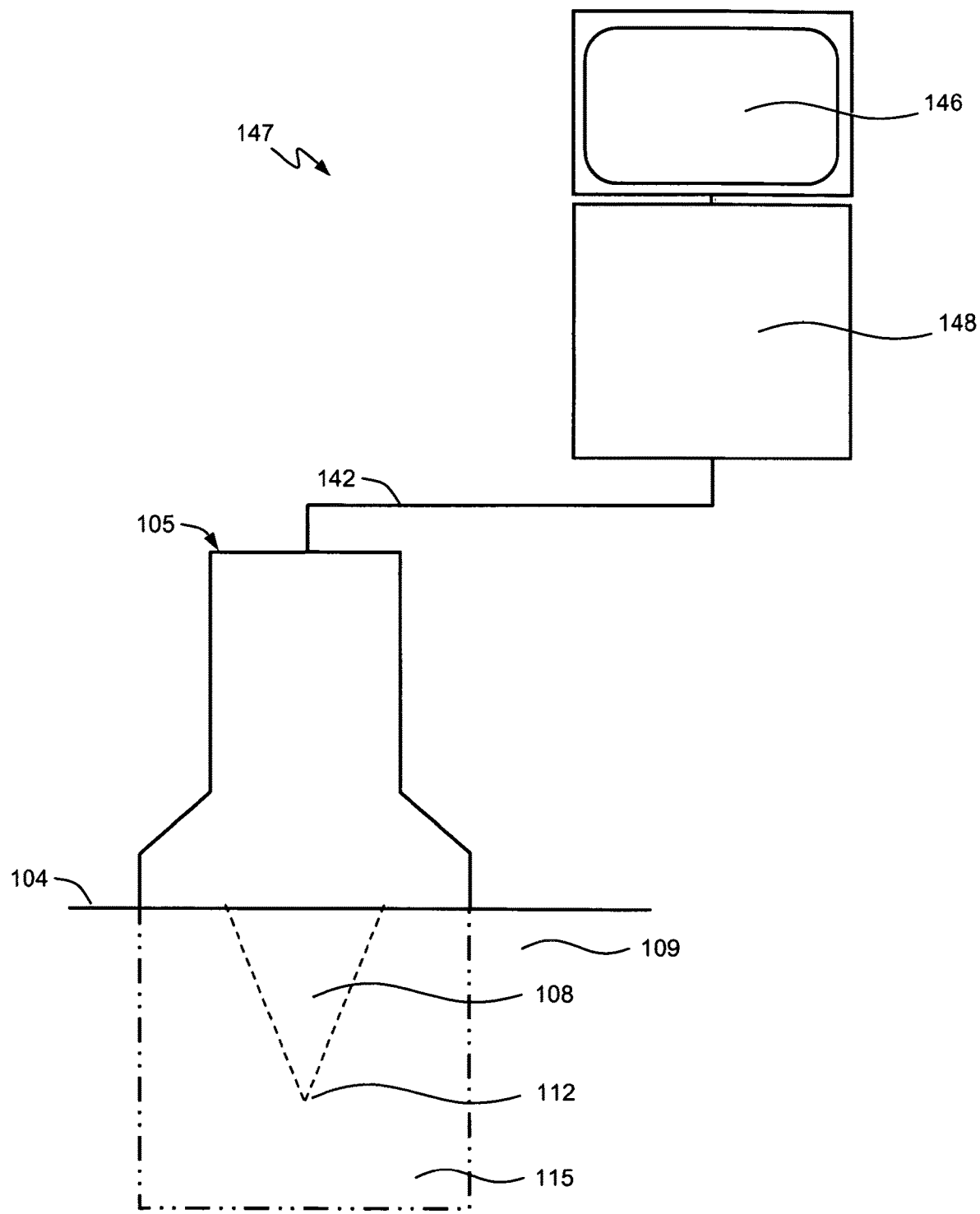
FIG. 15 illustrates a treatment system, according to various embodiments.

Now with reference to FIG. 15, extended field of view treatment system 147, according to various embodiments, is illustrated. In various embodiments, treatment system comprises controller 148, display 146, ultrasound probe 105, and interface 142 for communication between ultrasound probe 105 and controller 148. As described herein, interface 142 can be a wired connection, a wireless connection, and combinations thereof. Ultrasound probe 105 may be controlled and operated by controller 148, which also relays and processes images obtained by ultrasound probe 105 to display 146. In one embodiment, controller 148 is capable of coordination and control of the entire treatment process to achieve the desired therapeutic effect on ROI. For example, in one embodiment, controller 148 may comprise power source components, sensing and monitoring components, one or more RF driver circuits, cooling and coupling controls, and/or processing and control logic components. Controller 148 may be configured and optimized in a variety of ways with more or less subsystems and components to implement extended field of view treatment system 147 for controlled targeting of a portion of subcutaneous tissue 109, and the embodiments in FIG. 15 are merely for illustration purposes.

For example, for power sourcing components, controller 148 may comprise one or more direct current (DC) power supplies capable of providing electrical energy for the entire controller 148, including power required by a transducer electronic amplifier/driver. A DC current sense or voltage sense device may also be provided to confirm the level of power entering amplifiers/drivers for safety and monitoring purposes.

In one embodiment, amplifiers/drivers may comprise multi-channel or single channel power amplifiers and/or drivers. In one embodiment for transducer array configurations, amplifiers/drivers may also be configured with a beamformer to facilitate array focusing. An exemplary beamformer may be electrically excited by an oscillator/digitally controlled waveform synthesizer with related switching logic.

Power sourcing components may also comprise various filtering configurations. For example, switchable harmonic filters and/or matching may be used at the output of amplifier/driver to increase the drive efficiency and effectiveness. Power detection components may also be included to confirm appropriate operation and calibration. For example, electric power and other energy detection components may be used to monitor the amount of power entering ultrasound probe 105.

Various sensing and monitoring components may also be implemented within controller 148. For example, in one embodiment, monitoring, sensing, and interface control components may be capable of operating with various motion detection systems implemented within ultrasound probe 105, to receive and process information such as acoustic or other spatial and temporal information from ROI. Sensing and monitoring components may also comprise various controls, interfacing, and switches and/or power detectors. Such sensing and monitoring components may facilitate open-loop and/or closed-loop feedback systems within extended field of view treatment system 147.

In one embodiment, sensing and monitoring components may further comprise a sensor that may be connected to an audio or visual alarm system to prevent overuse of system. In this embodiment, the sensor may be capable of sensing the amount of energy transferred to the skin, and/or the time that extended field of view treatment system 147 has been actively emitting energy. When a certain time or temperature threshold has been reached, the alarm may sound an audible alarm, or cause a visual indicator to activate to alert the user that a threshold has been reached. This may prevent overuse of treatment system 147. In one embodiment, the sensor may be operatively connected to controller 148 and force controller 148, to stop emitting therapeutic ultrasound energy 108 from ultrasound probe 105.

Additionally, an exemplary controller 148 may further comprise a system processor and various digital control logic, such as one or more of microcontrollers, microprocessors, field-programmable gate arrays, computer boards, and associated components, including firmware and control software, which may be capable of interfacing with user controls and interfacing circuits as well as input/output circuits and systems for communications, displays, interfacing, storage, documentation, and other useful functions. System software may be capable of controlling all initialization, timing, level setting, monitoring, safety monitoring, and all other system functions required to accomplish user-defined treatment objectives. Further, various control switches, touch panels, multi-touch panels, capacitive and inductive switches, may also be suitably configured to control operation.

With reference again to FIG. 15, an exemplary treatment system 147 also may comprise display 146 capable of providing images of ROI in various embodiments where ultrasound energy may be emitted from ultrasound probe 105 in a manner for imaging. In one embodiment, display 146 is a computer monitor. Display 146 may be capable of enabling the user to facilitate localization of treatment area and surrounding structures, for example, identification of subcutaneous tissue layer 109. In an alternative embodiment, the user may know the location of the specific subcutaneous tissue layer 109 to be treated based at least in part upon prior experience or education and without display 146. In another embodiment, display 146 also includes a touch screen to allow user touch- or multi-touch input in a graphical user interface. In yet another embodiment display 146 is a 3-D display.

After localization, therapeutic ultrasound energy 108 is delivered at a depth, distribution, timing, and energy level to achieve the desired therapeutic effect at ROI to treat injury. Before, during and/or after delivery of therapeutic ultrasound energy 108, monitoring of the treatment area and surrounding structures may be conducted to further plan and assess the results and/or provide feedback to controller 148, and to a system operator via display 146.

Feedback information may be generated or provided by any one or more acoustical sources, such as B-scan images, A-lines, Doppler or color flow images, surface acoustic wave devices, hydrophones, elasticity measurement, or shear wave based devices. In addition, optical sources can also be utilized, such as video and/or infrared cameras, laser Doppler imagers, optical coherence tomography imagers, and temperature sensors. Further, feedback information can also be provided by semiconductors, such as thermistors or solid state temperature sensors, by electronic and electromagnetic sensors, such as impedance and capacitance measurement devices and/or thermocouples, and by mechanical sensors, such as stiffness gages, strain gages or stress measurement sensors, or any suitably combination thereof. Moreover, various other switches, acoustic or other sensing mechanisms and methods may be employed to enable transducer array 100 to be Acoustically coupled to one or more ROI.

Figure 16:
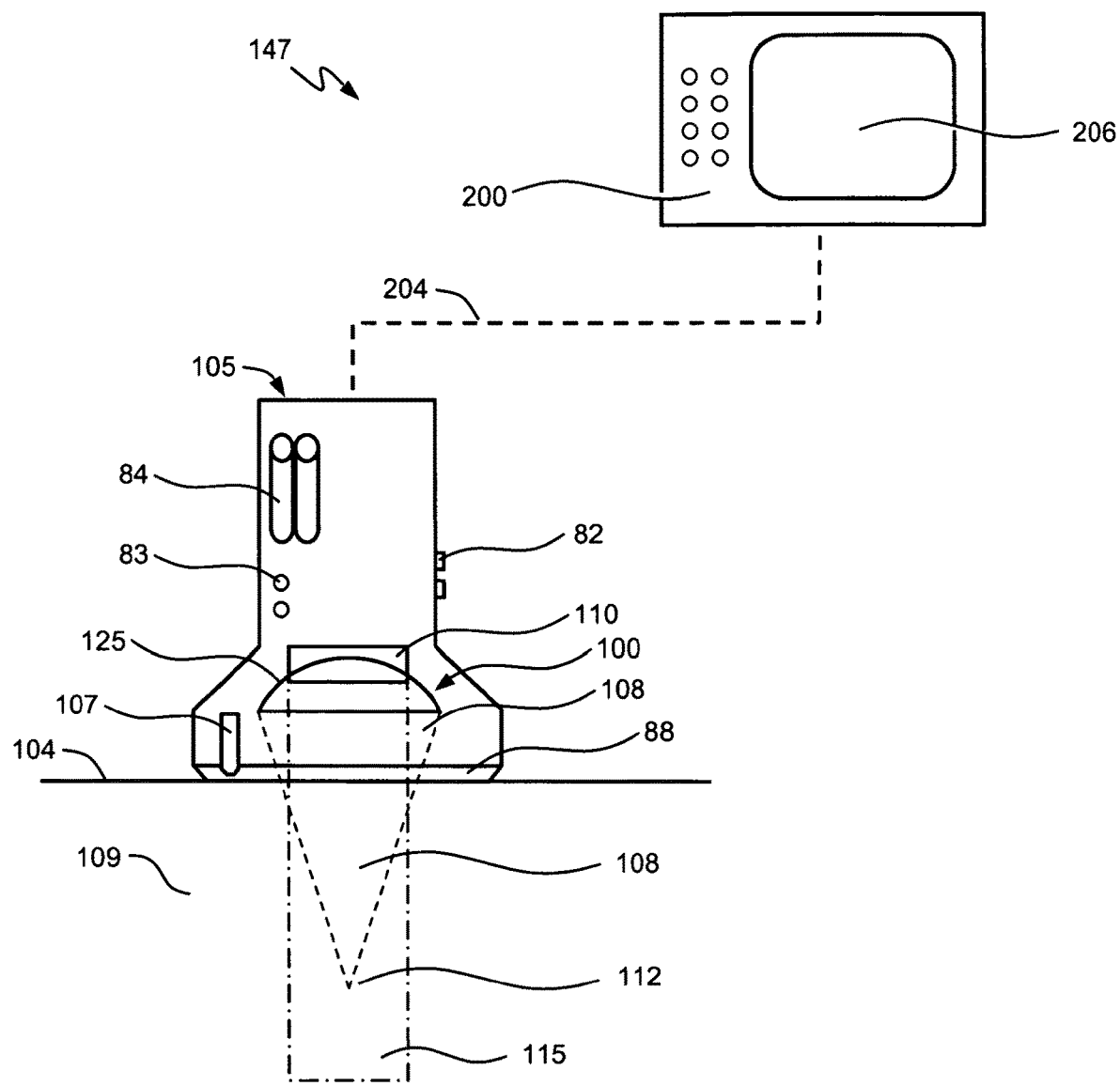
FIG. 16 illustrates a hand-held treatment system, according to various embodiments.

With reference to FIG. 16, a hand held ultrasound probe, according to various embodiments, is illustrated. In various embodiments, ultrasound transducer 105 comprises transducer array 100, as described herein, and may be controlled and operated by a hand-held format control system. An external battery charger can be used with rechargeable-type batteries 84 or the batteries 84 can be single-use disposable types, such as M-sized cells. Power converters produce voltages for powering a driver/feedback circuit with tuning network driving transducer array 100. Ultrasound probe 105 is coupled to skin surface 104 via one or more tips 88, which can be composed of at least one of a solid media, semi-solid, such as, for example, a gelatinous media, and liquid media equivalent to an acoustic coupling agent contained within a housing in tip. Tip 88 is coupled to skin surface 104 with an acoustic coupling agent. In addition, a microcontroller and timing circuits with associated software and algorithms provide control and user interfacing via a display or LED-type indicators 83, and other input/output controls 82, such as switches and audio devices. A storage element, such as an Electrically Erasable Programmable Read-Only Memory ("EEPROM"), secure EEPROM, tamper-proof EEPROM, or similar device can hold calibration and usage data. A motion mechanism with feedback can be controlled to scan the transducer array 100 in a linear pattern or a two-dimensional pattern or over a varied depth. Other feedback controls comprise capacitive, acoustic, or other coupling detection means, limiting controls, and thermal sensor. EEPROM can be coupled with at least one of tip 88, transducer array 100, thermal sensor, coupling detector, and tuning network. Data from EEPROM can be collected in controller 148 and connected to treatment data.

In one embodiment, data from EEPROM can be downloaded to a user's computer via any interface type, such as, for example, a USB interface, a RS 232 interface, a IEEE interface, a fire-wire interface, a blue tooth interface, an infrared interface, a 802.1 interface, via the web, and the like. Downloadable data can include hours of use, frequency during use, power levels, depths, codes from tips used, error codes, user ID, and other such data. The data can be parsed by user ID so more than one user can track user data. Similarly, EEPROM can be interfaced, using any of the methods or devices described herein, to a computer or the web to receive software updates. Still further, EEPROM can be interfaced, using any of the methods or devices described herein, to a computer or the web for at least one of diagnosis, trouble shooting, service, repair, and combinations thereof.

In some embodiments, ultrasound probe 105 comprises imaging transducer 110. In some embodiments, ultrasound probe 105 comprises position sensor 107, as described herein. In some embodiments, therapy transducer array 100 is operable for emitting therapeutic ultrasound energy 108 and imaging transducer 110 is operable for imaging 115, as described herein.

As illustrated in FIG. 16, ultrasound probe 105 can be in communication with wireless device 200 via wireless interface 204. Typically, wireless device 200 has display 206 and a user interface such as, for example, a keyboard. Examples of wireless device 200 can include but are not limited to: personal data assistants ("PDA"), cell phone, iphone, ipad, computer, laptop, netbook, or any other such device now known or developed in the future. Examples of wireless interface 204 include but are not limited to any wireless interface described herein and any such wireless interface now known or developed in the future. Accordingly, ultrasound probe 105 comprises any hardware, such as, for example, electronics, antenna, and the like, as well as, any software that may be used to communicate via wireless interface 204.

In various embodiments, device 200 can display an image generated by handheld probe 105. In various embodiments, device 200 can control handheld ultrasound probe 105. In various embodiments, device 200 can store data generated by handheld ultrasound probe 105.

In various embodiments, therapy transducer array 100, imaging transducer array 110, and optionally, position sensor 107 can held within enclosure 78. In one embodiment, enclosure 78 is designed for comfort and control while used in an operator's hand. Enclosure 78 may also contain various electronics, such as, for example, EEPROM, interface connection, motion mechanisms, /or ram for holding programs, and combinations thereof.

Therapeutic ultrasound energy 108 from therapy transducer array 100 may be spatially and/or temporally controlled at least in part by changing the spatial parameters of therapy transducer array 100, such as the placement, distance, treatment depth and therapy transducer array 100 structure, as well as by changing the temporal parameters of therapy transducer array 100, such as the frequency, drive amplitude, and timing, with such control handled via controller in hand-held assembly of ultrasound probe 105. In various embodiments, ultrasound probe 105 comprises a transducer array 100 capable of emitting therapeutic ultrasound energy 108 into ROI. This may heat ROI at a specific depth to target tissue causing that tissue to be ablated, micro-ablated, coagulated, incapacitated, partially incapacitated, rejuvenated, shortened, paralyzed, or removed.

In various embodiments, rejuvenation is a reversal or an attempt to reverse the aging process. Rejuvenation can be the reversal of aging and is namely repair of the damage that is associated with aging or replacement of damaged tissue with new tissue. In some embodiments, cosmetic enhancement can refer to procedures, which may not be medically necessary but can be used to improve or change the appearance of a portion of the body. For example, a cosmetic enhancement can be a procedure but not limited to procedures that are used to improve or change the appearance of a nose, eyes, eyebrows and/or other facial features, or to improve or change the appearance and/or the texture and/or the elasticity of skin, or to improve or change the appearance of a mark or scar on a skin surface, or to improve or change the appearance and/or the content of fat near a skin surface, or the targeting of a gland to improve or change the appearance a portion of the body. In at least one embodiment, cosmetic enhancement is a non-surgical and non-invasive procedure. In various embodiments, cosmetic enhancement provides rejuvenation to at least one portion of the body.

In some embodiments, methods of cosmetic enhancement can increase elasticity of skin by thinning a dermis layer, thereby rejuvenating a portion of skin. In some embodiments, methods of cosmetic enhancement can stimulate initiation of internal body resources for the purpose of repairing an injury and/or cell deficiency.

The following patents and patent applications are incorporated by reference: US Patent Application Publication No. 20050256406, entitled "Method and System for Controlled Scanning, Imaging, and/or Therapy" published Nov. 17, 2005; US Patent Application Publication No. 20060056664, entitled "System and Method for Variable Depth Ultrasound Treatment" published Mar. 16, 2006; US Patent Application Publication No. 20060084891, entitled Method and System for Ultra-High Frequency Ultrasound Treatment" published Apr. 20, 2006; U.S. Pat. No. 7,530,958, entitled "Method and System for Combined Ultrasound Treatment" issued May 12, 2009; US Patent Application Publication No. 2008071255, entitled "Method and System for Treating Muscle, Tendon, Ligament, and Cartilage Tissue" published Mar. 20, 2008; U.S. Pat. No. 6,623,430, entitled "Method and Apparatus for Safely Delivering Medicants to a Region of Tissue Using Imaging, Therapy, and Temperature Monitoring Ultrasonice System, issued Sep. 23, 2003; U.S. Pat. No. 7,571,336, entitled "Method and System for Enhancing Safely with Medical Peripheral Device by Monitoring if Host Computer is AC Powered" issued Aug. 4, 2009; and US Patent Application Publication No. 20080281255, entitled "Methods and Systems for Modulating Medicants Using Acoustic Energy" published Nov. 13, 2008.

It is believed that the disclosure set forth above encompasses at least one distinct invention with independent utility. While the invention has been disclosed in the exemplary forms, the specific embodiments thereof as disclosed and illustrated herein are not to be considered in a limiting sense as numerous variations are possible. The subject matter of the inventions includes all novel and non-obvious combinations and sub combinations of the various elements, features, functions and/or properties disclosed herein.

Various embodiments and the examples described herein are exemplary and not intended to be limiting in describing the full scope of compositions and methods of this invention. Equivalent changes, modifications and variations of various embodiments, materials, compositions and methods may be made within the scope of the present invention, with substantially similar results.

The invention claimed is:

1. A method of ultrasound treatment using a hand-held probe coupled to a treatment region, the hand-held probe including a housing containing or coupled to a therapy ultrasound transducer, an imaging ultrasound transducer, and a position sensor, the method comprising:
   a) acquiring, using the imaging ultrasound transducer, a first image of the treatment region;
   b) monitoring, using the position sensor, a position of the housing versus time;
   c) subsequent to the acquiring of step a), moving the housing, thereby coupling the housing to an extended treatment region;
   d) subsequent to the moving of step c), acquiring, using the imaging ultrasound transducer, a second image of the extended treatment region;
   e) forming and correlating the first image and the second image to create an extended field of view image of the treatment region and the extended treatment region; and
   f) delivering, using the therapy ultrasound transducer, directed therapeutic ultrasound energy into the treatment region or the extended treatment region, wherein the delivering directed therapeutic ultrasound energy is controlled using the position of the housing versus time.

2. The method according to claim 1, wherein the delivering of step f) initiates at least one ultrasound induced biological effect in the treatment region or the extended treatment region.

3. The method according to claim 1, wherein the directed therapeutic ultrasound energy is spherically focused, cylindrically focused, multi-focused, unfocused, or defocused.

4. The method according to claim 1, wherein the position sensor is an optical position sensor.

5. The method according to claim 1, further comprising displaying the first image, the second image, or the extended field of view image.

6. The method according to claim 1, further comprising dynamically targeting an additional treatment region with directed ultrasound energy based on the monitoring of step b).

7. The method according to claim 1, further comprising creating thermally or mechanically induced ultrasound bioeffects with directed ultrasound energy at or adjacent to the treatment region or the extended treatment region, the thermally or mechanically induced ultrasound bioeffects selected from the group consisting of effects of heating, coagulation, ablation, cavitation, streaming, radiation force, increased perfusion, inflammation, generation of heat shock proteins, and initiation of healing cascade.

8. The method according to claim 1, the treatment region comprising a non-flat surface.

9. The method according to claim 1, the hand-held probe further comprising a tissue contact sensor, the method further comprising:
   g) monitoring, using the tissue contact sensor, to determine if the therapy ultrasound transducer or the imaging ultrasound transducer are coupled to the treatment region or the extended treatment region.

10. The method according to claim 9, wherein the tissue contact sensor is a capacitive contact sensor and the monitoring of step g) includes measuring a capacitance of a skin surface above the treatment region or the extended treatment region.

11. The method according to claim 9, wherein the monitoring of step g) is initiated by pressing the hand-held probe against a skin surface above the treatment region or the extended treatment region.

12. The method according to claim 1, wherein the delivering of step f) includes delivering pulses of therapeutic ultrasound energy into the treatment region or the extended treatment region, wherein the pulses of therapeutic ultrasound energy are separated by a pre-determined distance.

13. The method according to claim 1, wherein the monitoring of step b) includes determining a speed of motion of the hand-held probe and the delivering of step f) is further controlled using the speed of motion of the hand-held probe.

14. The method according to claim 1, wherein delivery of additional directed ultrasound energy into the treatment region or the extended treatment region is prevented when the housing crosses over a position of the housing during a previous delivery of directed therapeutic ultrasound energy.

* * * * *

UNITED STATES PATENT AND TRADEMARK OFFICE
CERTIFICATE OF CORRECTION

| | |
|---|---|
| PATENT NO. | : 10,905,900 B2 |
| APPLICATION NO. | : 15/368220 |
| DATED | : February 2, 2021 |
| INVENTOR(S) | : Peter G. Barthe et al. |

It is certified that error appears in the above-identified patent and that said Letters Patent is hereby corrected as shown below:

In the Specification

Column 4, Line 67, "laver" should be --layer--.

Column 9, Line 55, "tens" should be --lens--.

Column 12, Line 19, "interlacing" should be --interfacing--.

Figure 3:
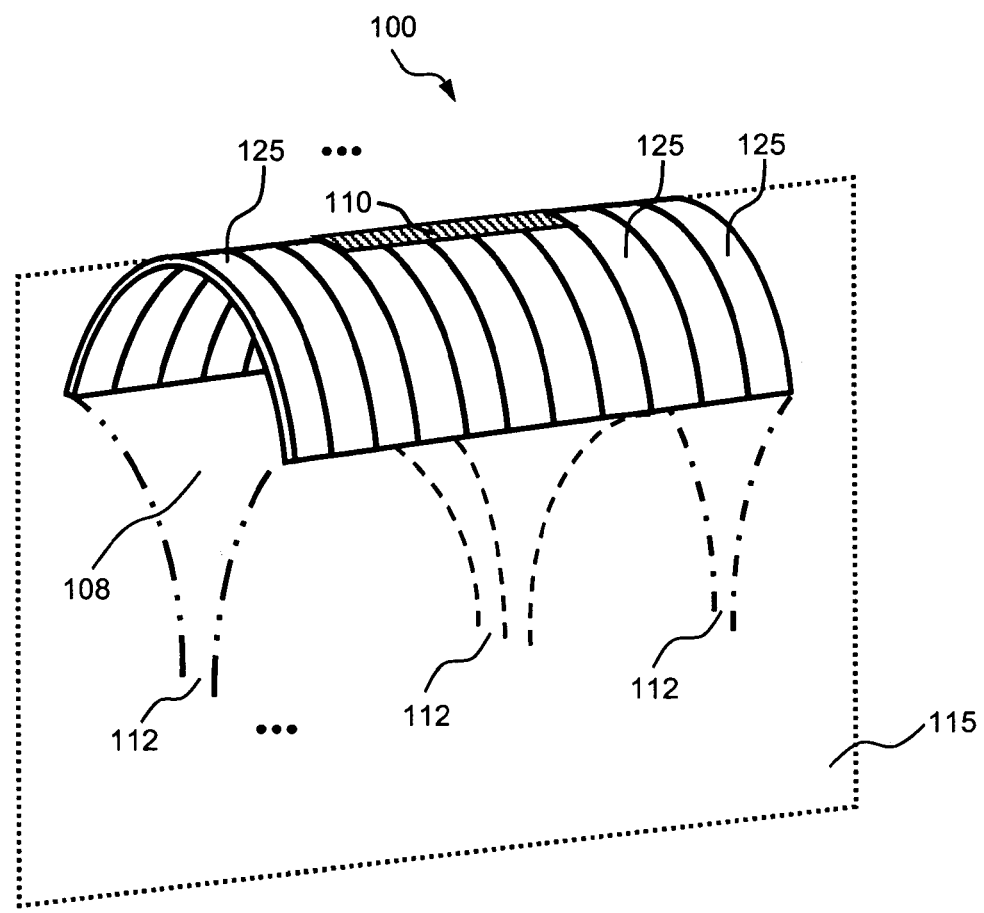
FIG. 3 illustrates a transducer array, according to various embodiments.

Column 13, Line 4, "FIG. 1" should be --FIG. 3--.

Column 13, Line 12, "123" should be --125--.

Column 14, Line 13, "1258" should be --125B--.

Column 14, Line 51, "indirection" should be --in direction--.

Column 16, Line 30, "prone" should be --probe--.

Column 16, Line 33, "con" should be --can--.

Column 18, Line 67, "indirection" should be --in direction--.

Column 21, Line 6, "Acoustically" should be --acoustically--.

Column 23, Line 2, "20060056664" should be --20060058664--.

Signed and Sealed this
Fourteenth Day of June, 2022

Katherine Kelly Vidal
*Director of the United States Patent and Trademark Office*